US010688151B2

(12) United States Patent
Trepel et al.

(10) Patent No.: US 10,688,151 B2
(45) Date of Patent: Jun. 23, 2020

(54) PEPTIDES HAVING SPECIFICITY FOR THE LUNGS

(71) Applicant: Boehringer Ingelheim International GmbH, Ingelheim am Rhein (DE)

(72) Inventors: Martin Trepel, Hamburg (DE); Jakob Koerbelin, Hamburg (DE); Stefan Michelfelder, Freiburg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/911,197

(22) PCT Filed: Aug. 6, 2014

(86) PCT No.: PCT/EP2014/066892
§ 371 (c)(1),
(2) Date: Feb. 9, 2016

(87) PCT Pub. No.: WO2015/018860
PCT Pub. Date: Feb. 12, 2015

(65) Prior Publication Data
US 2016/0175389 A1 Jun. 23, 2016

(30) Foreign Application Priority Data
Aug. 9, 2013 (DE) .................. 10 2013 215 817

(51) Int. Cl.
A61K 38/08 (2019.01)
C12N 15/00 (2006.01)
C12N 5/02 (2006.01)
C12N 5/07 (2010.01)
A61K 38/04 (2006.01)
C07K 5/00 (2006.01)
C07K 7/00 (2006.01)
C07K 16/00 (2006.01)
C07K 17/00 (2006.01)
C07H 21/02 (2006.01)
A61K 38/16 (2006.01)
C12N 15/86 (2006.01)
C07K 14/005 (2006.01)
C12N 7/00 (2006.01)

(52) U.S. Cl.
CPC .......... *A61K 38/162* (2013.01); *C07K 14/005* (2013.01); *C12N 7/00* (2013.01); *C12N 15/86* (2013.01); *C07K 2319/33* (2013.01); *C12N 2750/14122* (2013.01); *C12N 2750/14133* (2013.01); *C12N 2750/14143* (2013.01); *C12N 2750/14171* (2013.01); *C12N 2799/025* (2013.01); *C12N 2810/40* (2013.01)

(58) Field of Classification Search
None
See application file for complete search history.

(56) References Cited

U.S. PATENT DOCUMENTS

| 8,007,780 B2 * | 8/2011 | Arbetman | A61K 48/0075 |
| | | | 424/93.1 |
| 2007/0172460 A1 * | 7/2007 | Kleinschmidt | C12N 15/1037 |
| | | | 424/93.2 |

FOREIGN PATENT DOCUMENTS

| DE | 102014207498 | 10/2015 |
| WO | 2004/083441 A2 | 9/2004 |
| WO | 2010127097 | 11/2010 |
| WO | 2015158749 | 10/2015 |

OTHER PUBLICATIONS

Korbelin et al. "Pulmonary Targeting of Adeno-associated Viral Vectors by Next-generation Sequencing-guided Screening of Random Capsid Displayed Peptide Libraries" Mol. Ther. 24:1050-1061. (Year: 2016).*
UniProt Accession No. Q47W67 (Year: 2005).*
Muller et al. "Random peptide libraries displayed on adeno-associated virus to select for targeted gene therapy vectors" Nature Biotech. 21:1040-1046. (Year: 2003).*
Barst et al., Diagnosis and Differential Assessment of Pulmonary Arterial Hypertension, 2004 Journal of the American College of Cardiology, vol. 43, No. 12 pp. 40-47 (8 pages).
McLaughlin et al., ACCF/AHA 2009 Expert Consensus Document on Pulmonary Hypertension, A Report of the American College of Cardiology Foundation Task Force on Expert Consensus Documents and the American Heart Association, Circulation, 2009, 119: 2250-2294 (47 pages).
Stenmark et al., Animal models of pulmonary arterial hypertension: the hope for etiological discovery and pharmacological cure, Am J Physiol Lung Cell Mol Physiol, Sep. 11, 2009, 297: 1013-1032 (20 pages).
Friedman et al., Obesity and Pulmonary Hypertension: A Review of PathophysiologicMechanisms, 2012 Journal of Obesity, vol. 2012: 505274 (9 pages).
Chin et al., The right ventricle in pulmonary hypertension, Coronary Artery Disease, 2005, vol. 16 No. 1: 13-18 (6 pages).

(Continued)

Primary Examiner — James H Alstrum-Acevedo
Assistant Examiner — Zachary J Miknis
(74) Attorney, Agent, or Firm — Hovey Williams LLP

(57) ABSTRACT

The invention relates to a peptide, polypeptide, or protein that binds specifically to cells of the lung endothelium. The peptide, polypeptide, or protein can be a component of a viral capsid and can be used to lead a recombinant viral vector selectively to the lung endothelial tissue after systemic administration to a subject and to ensure tissue-specific expression of one or more transgenes there. The invention thus further relates to a recombinant viral vector, preferably an AAV vector, which comprises a capsid comprising the peptide, polypeptide, or protein according to the invention and which comprises at least one transgene packaged in the capsid. The viral vector is suitable in particular for the therapeutic treatment of a lung disorder or a lung disease. The invention further relates to cells and pharmaceutical compositions which comprise the viral vector according to the invention.

25 Claims, 5 Drawing Sheets
Specification includes a Sequence Listing.

(56) References Cited

OTHER PUBLICATIONS

Hemnes et al., Right heart function and haemodynamics in pulmonary hypertension, International Journal of Clinical Practice (Suppl. 160), Jul. 2008,11-19 (9 pages).

Humbert et al., Update in Pulmonary Hypertension 2008, Am J Respir Crit Care Med, Jan. 26, 2009, vol. 179, pp. 650-656 (7 pages).

Simonneau et al., Updated Clinical Classification of Pulmonary Hypertension, Journal of the American College of Cardiology, 2009, vol. 54, No. 1, Suppl S: 43-54 (12 pages).

Humbert et al., Pulmonary Arterial Hypertension in France, Am J Respir Crit Care Med, Feb. 2, 2006, vol. 173 pp. 1023-1030 (8 pages).

Tenenbaum et al., Evaluation of Risks Related to the Use of Adeno-Associated Virus-Based Vectors, 2003, Current Gene Therapy, 2003, vol. 3, No. 6: 545-565 (22 pages).

Work et al., Vascular Bed-Targeted in Vivo Gene Delivery Using Tropism-Modified Adeno-associated Viruses, Molecular Therapy, Apr. 2006, vol. 13, No. 4: 683-693 (11 pages).

Shi et al., Brief Report, Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism, Human Gene Therapy, Mar. 2006, 17: 353-361 (9 pages).

Michelfelder et al., Successful Expansion but Not Complete Restriction of Tropism of Adeno-Associated Virus by In Vivo Biopanning of Random Virus Display Peptide, Apr. 9, 2009, PLoS One, 4(4): e5122. doi:10.1371/journal.pone.0005122 (13 pages).

Shi et al., RGD Inclusion in VP3 Provides Adeno-Associated Virus Type 2 (AAV2)-Based Vectors with a Heparan Sulfate-Independent Cell Entry Mechanism, Molecular Therapy, Apr. 2003, vol. 7, No. 4: 515-525 (11 pages).

Loiler et al., Targeting recombinant adeno-associated virus vectors to enhance gene transfer to pancreatic islets and liver, Gene Therapy, 2003, 10: 1551-1558 (8 pages).

Rabinowitz et al., Insertional Mutagenesis of AAV2 Capsid and the Production of Recombinant Virus, Virology, 1999, 265: 274-285 (12 pages).

Wu et al., Mutational Analysis of the Adeno-Associated Virus Type 2 (AAV2) Capsid Gene and Construction of AAV2 Vectors with Altered Tropism, Journal of Virology, Sep. 2000, vol. 74, No. 18: 8635-8647 (13 pages).

Shi et al., 2001, Insertional Mutagenesis of the Adeno-Associated Virus Type 2 (AAV2) Capsid Gene and Generation of AAV2 Vectors Targeted to Alternative Cell-Surface Receptors, Human Gene Therapy, Sep. 20, 2001, 12: 1697-1711 (15 pages).

Warrington et al., Adeno-Associated Virus Type 2 VP2 Capsid Protein Is Nonessential and Can Tolerate Large Peptide Insertions at Its N Terminus, Journal of Virology, Jun. 2004, vol. 78, No. 12: 6595-6609 (15 pages).

Girod et al., Genetic capsid modifications allow efficient re-targeting of adeno-associated virus type 2, Nature Medicine, Sep. 1999, vol. 5, No. 9: 1052-1056 (5 pages).

Grifman et al., Incorporation of Tumor-Targeting Peptides into Recombinant Adeno-associated Virus Capsids, Molecular Therapy, Jun. 2001, vol. 3, No. 6: 964-975 (12 pages).

Opie et al., Identification of Amino Acid Residues in the Capsid Proteins of Adeno-Associated Virus Type 2 That Contribute to Heparan Sulfate Proteoglycan Binding, Journal of Virology, Jun. 2003, vol. 77, No. 12: 6995-7006 (12 pages).

Kern et al., Identification of a Heparin-Binding Motif on Adeno-Associated Virus Type 2 Capsids, Journal of Virology, Oct. 2003, vol. 77, No. 20: 11072-11081 (10 pages).

Russell et al., Infectious Clones and Vectors Derived from Adeno-Associated Virus (AAV) Serotypes Other Than AAV Type 2, Journal of Virology, Jan. 1998, vol. 72, No. 1: 309-319 (11 pages).

Muller, et al., Random peptide libraries displayed on adeno-associated virus to select for targeted gene therapy vectors, 2003, Nature Biotechnology, Sep. 2003, vol. 21, No. 9, pp. 1040-1046 (7 pages).

Waterkamp et al., Isolation of targeted AAV2 vectors from novel virus display libraries, The Journal of Gene Medicine, Sep. 6, 2006, 8:1307-1319 (13 pages).

Xiao et al., Production of High-Titer Recombinant Adeno-Associated Virus Vectors in the Absence of Helper Adenovirus, Journal of Virology, Mar. 1998, vol. 72, No. 3:2224-2232 (9 pages).

Zolotukhin et al., Recombinant adeno-associated virus purification using novel methods improves infectious titer and yield, Gene Therapy, Feb. 12, 1999, 6, 973-985 (13 pages).

McCarty et al., Self-complementary recombinant adeno-associated virus (scAAV) vectors promote efficient transduction independently of DNA synthesis, Gene Therapy, May 22, 2001, 8, 1248-1254 (7 pages).

Michelfelder et al., Vectors selected from adeno-associated viral display peptide libraries for leukemia cell-targeted cytotoxic gene therapy, Experimental Hematology 35, Jul. 23, 2007, 1766-1776 (11 pages).

Rohr et al., Quantitative real-time PCR for titration of infectious recombinant AAV-2 particles, Journal of Virological Methods, Apr. 12, 2005, 127, 40-45 (6 pages).

Database UniProt [Online] Sep. 13, 2005 (Sep. 13, 2005), "RecName: Full=Sugar fermentation stimulation protein homolog;", EBI accession No. UNIPROT:Q47W67 Database accession No. Q47W67 (1 page).

Michelfelder et al: Peptide Ligands Incorporated into the Threefold Spike Capsid Domain to Re-Direct Gene Transduction of AAV8 and AAV9 In Vivo, PLOS ONE, vol. 6, No. 8, Aug. 5, 2011 (Aug. 5, 2011), pp. e23101.

Ying et al: Heart-targeted adeno-associated viral vectors selected by in vivo biopanning of a random viral display peptide library, Gene Therapy, vol. 17, No. 8 , Apr. 15, 2010 (Apr. 15, 2010) , pp. 980-990 (11 pages).

Michelfelder et al: "Successful Expansion but Not Complete Restriction of Tropism of Adeno-Associated Virus by In Vivo Biopanning of Random Virus Display Peptide Libraries", PLOS ONE, vol. 4, No. 4, Apr. 9, 2009 (Apr. 9, 2009), pp. e5122 (13 pages).

International Search Report in Corresponding PCT/EP2014/066892, dated Nov. 5, 2014, English Translation (3 pages).

Written Opinion of the International Searching Authority in Corresponding PCT/EP2014/066892, dated Nov. 5, 2014, English Translation (6 pages).

Internet-Search dated Feb. 19, 2014 Major coat protein VP1 [Adeno-associated virus—21 Accession No. YP-680426 (1 page).

Internet-Search dated Feb. 19, 2014 Sequence comparison SEQ ID No. 9 and YP-680426 (3 pages).

Search Report and Written Opinion in PCT Patent Application Serial No. PCT/EP2015/058123 dated Dec. 11, 2015, 17 pages (translation attached), corresponding to co-pending national stage U.S. Appl. No. 15/303,950.

Allard, et al., "Characterization of rat spinal cord receptors to FLFQPQRFamide, a mammalian morphine modulating peptide: a binding study", Brain Res., Oct. 23, 1989, vol. 500, issue 1-2, pp. 169-176 (abstract attached).

Benyhe, et al., "Met-5-enkephalin-Arg-6-Phe-7, an endogenous neuropeptide, binds to multiple opioid and nonopioid sites in rat brain", J. Neurosci. Res., May 1, 1997, vol. 48, issue 3, pp. 249-258 (abstract attached).

Meunier, et al., "Isolation and structure of the endogenous agonist of opioid receptor-like ORL1 receptor", Nature, vol. 377, Oct. 12, 1995, pp. 532-535 (abstract attached).

Igwe, et al., "Specific Binding of Substance P Amino-terminal Heptapeptide [SP( l-7)] to Mouse Brain and Spinal Cord Membranes", J. Neurosci., vol. 10, issue 11, Nov. 1990, pp. 3653-3663.

Bartlett, et al., "Selective and rapid uptake of adeno-associated virus type 2 in brain", Hum. Gene. Ther., vol. 9, issue 8, May 20, 1998, pp. 1181-1186 (abstract attached).

XP002740760, "Talaromyces stipitatus ATCC 10500 phenylacetyl-CoA ligase, putative", Dec. 29, 2008 (abstract attached).

(56) References Cited

OTHER PUBLICATIONS

Kaplitt et al., "Safety and tolerability of gene therapy with an adeno-associated virus (AAV) borne GAD gene for Parkinson's disease: an open label, phase I trial", Jun. 23, 2007, Lancet, vol. 369, issue 9579, pp. 2097-2105.

Gray et al., "Directed Evolution of a Novel Adeno-associated Virus (AAV) Vector That Crosses the Seizure-compromised Blood-Brain Barrier (BBB)", Mar. 2010, Mol. Ther., vol. 18, issue 3, pp. 570-578.

Shevtsova et al., "Promoters and serotypes: targeting of adeno-associated virus vectors for gene transfer in the rat central nervous system in vitro and in vivo", 2005, Exp. Physiol., vol. 90, issue 1, pp. 53-59.

Gray et al., "Optimizing Promoters for Recombinant Adeno-Associated Virus-Mediated Gene Expression in the Peripheral and Central Nervous System Using Self-Complementary Vectors", Sep. 2011, Hum. Gene Ther., vol. 22, issue 9, pp. 1143-1153.

Aebischer et al., "Intrathecal delivery of CNTF using encapsulated genetically modified xenogenic cells in amyotrophic lateral sclerosis patients", Jun. 1996, Nat. Med., vol. 2, issue 6, pp. 696-699.

McCown et al., "Differential and persistent expression patterns of CNS gene transfer by an adeno-associated virus (AAV) vector", 1996, Brain Res., vol. 713, issue 1-2, pp. 99-107.

During et al., "In vivo expression of therapeutic human genes for dopamine production in the caudates of MPTP-treated monkeys using an AAV vector", 1998, Gene Ther., vol. 5, issue 6, pp. 820-827.

Kalburgi et al., "Recent Gene Therapy Advancements for Neurological Diseases", Feb. 2013, Discov. Med., vol. 15, issue 81, pp. 111-119.

Alonso et al., "Focal Delivery of AAV2/1-transgenes Into the Rat Brain by Localized Ultrasound-induced BBB Opening", 2013, Mol. Ther. Nucleic Acids, vol. 2, 7 pages.

Ruthledge et al., "Infectious Clones and Vectors Derived from Adeno-Associated Virus (AAV) Serotypes Other Than AAV Type 2", Jan. 1998, J. Virol., vol. 72, issue 1, pp. 309-319.

Urabe et al., "Insect Cells as a Factory to Produce Adeno-Associated Virus Type 2 Vectors", Nov. 1, 2002, Hum. Gene Ther., vol. 13, pp. 1935-1943.

Kohlbrenner et al., "Successful Production of Pseudotyped rAAV Vectors Using a Modified Baculovirus Expression System", Dec. 2005, Mol. Ther., vol. 12, issue 6, pp. 1217-1225.

Chen, "Intron Splicing-mediated Expression of AAV Rep and Cap Genes and Production of AAV Vectors in Insect Cells", May 2008, Mol. Ther., vol. 16, issue 5, pp. 924-930.

Office Action in related German Patent Application Serial No. 102014207498.3, dated Sep. 8, 2014 (English translation attached), corresponding to U.S. Appl. No. 15/303,950.

XP_002487045, "Talaromyces Stipitatus ATCC 10500", Oct. 1, 2007.

Korbelin, et al., "Pulmonary Targeting of Adeno-associated Viral Vectors by Next-generation Sequencing-guided Screening of Random Capsid Displayed Peptide Libraries" American Society of Gene & Cell Therapy, Jun. 2016, vol. 24, issue 6, pp. 1050-1061.

Office Action corresponding to U.S. Appl. No. 15/303,950, dated Aug. 25, 2017 (8 pages).

Office Action corresponding to U.S. Appl. No. 15/303,950, dated Dec. 22, 2017 (15 pages).

Office Action corresponding to U.S. Appl. No. 15/303,950, dated Jun. 26, 2018 (10 pages).

\* cited by examiner

1st Round
(SEQ ID NO:22) GQIGGSA (SEQ ID NO:22) GQIGGSA (SEQ ID NO:23) LTRAAGV (SEQ ID NO:24) VPWSPSV

2nd Round
NDVRAVS (SEQ ID NO:25)

NDVRAVS (SEQ ID NO:25)

NQVGSXS (SEQ ID NO:26)

NSVAATA (SEQ ID NO:27)

NSVAATA (SEQ ID NO:27)

PRTLAEL (SEQ ID NO:28)

TLREQSP (SEQ ID NO:29)

3rd Round
(SEQ ID NO:3) ADGVMWL (SEQ ID NO:30) EGRLGAG (SEQ ID NO:30) EGRLGAG (SEQ ID NO:30) EGRLGAG (SEQ ID NO:2) ESGHGYF (SEQ ID NO:31) GGRPMHE (SEQ ID NO:32) NSVNDRS (SEQ ID NO:33) PRSVDLS (SEQ ID NO:34) RGDVTKE (SEQ ID NO:35) QGDLGLS

4th Round
ADGVMWL (SEQ ID NO:3)

ADGVMWL (SEQ ID NO:3)

ESGHGYF (SEQ ID NO:2)

ESGHGYF (SEQ ID NO:2)

ESGHGYF (SEQ ID NO:2)

ESGHGYF (SEQ ID NO:2)

ESGHGYF (SEQ ID NO:2)

GEVYVSF (SEQ ID NO:4)

NNVRTSE (SEQ ID NO:5)

Fig. 2

PEPTIDES HAVING SPECIFICITY FOR THE LUNGS

RELATED APPLICATIONS

This application is the National Stage of International Patent Application No. PCT/EP2014/066892, filed Aug. 6, 2014, which is hereby incorporated by reference in its entirety, and which claims priority to German Patent Application No. DE 10 2013 215 817.3, filed Aug. 9, 2013.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

The invention relates to a peptide, polypeptide, or protein that binds specifically to cells of the lung endothelium. The peptide, polypeptide, or protein can be a component of a viral capsid and can be used to lead a recombinant viral vector selectively to the lung endothelial tissue after systemic administration to a subject and to ensure tissue-specific expression of one or more transgenes there. The invention thus further relates to a recombinant viral vector, preferably an AAV vector, which comprises a capsid comprising the peptide, polypeptide, or protein according to the invention and which comprises at least one transgene packaged in the capsid. The viral vector is suitable in particular for the therapeutic treatment of a lung disorder or a lung disease. The invention further relates to cells and pharmaceutical compositions which comprise the viral vector according to the invention.

BACKGROUND OF THE INVENTION

Pulmonary hypertension is a serious chronic lung disease which regularly leads to death if untreated. The term applies to diseases of various causes, which are characterized by a structural change in the pulmonary vasculature, and in which there is an increase in blood pressure in the pulmonary arterial system to more than 25 mm Hg [1]. This usually results, in affected patients, in stress-dependent shortness of breath, and general loss of capacity. Disease progression leads to a narrowing of vessels resulting from a transformation (remodeling) and thickening of all three layers of the vessel wall, i.e. intima, media and adventitia [2]. This often leads to resting dyspnea, global respiratory insufficiency, and the congestive syndromes associated with right-sided heart failure and in the long-term to heart failure. Pulmonary arterial hypertension is a particularly severe form of pulmonary hypertension in which the median survival from diagnosis is only about three years [3], and diagnosis is often made very late due to the initially mild symptoms.

Several animal models that functionalize different disease characteristics are available for investigating the mechanisms of pulmonary hypertension, and for pre-clinical treatment studies. These include both inducible models (hypoxia, monocrotaline, or antigens, for example) and transgenic models, wherein the selection of a suitable model depends on the research question being examined [4].

Not all possible causes of the various forms of pulmonary arterial hypertension have been explained to date. Nevertheless, there are several well-known and therapeutically relevant factors. For example, in cases of idiopathic pulmonary arterial hypertension, the increased release of vasoconstrictive factors is discussed [5-7], while in many cases of familial pulmonary arterial hypertension, mutations of BMPR2 [8] or the Activin receptor-like kinase 1 (ALK1) gene [9] are considered likely causes.

The development of new therapeutic options for the treatment of pulmonary hypertension or pulmonary arterial hypertension is an urgent need. Such a development could be the transfer of therapeutic genes into lung tissue, and more particularly into the pulmonary endothelium. Vectors that allow a specific and efficient gene transfer into the pulmonary endothelium have not yet been described in the prior art. Gene therapy using viral vectors is a promising treatment option for diseases that do not respond at all, or not adequately, to conventional treatment. This approach is based on the introduction of therapeutic genes into the organism being treated, by means of viruses which have been modified in such a manner that they have the sequence of the corresponding gene in their genome. Viral vectors which have already been used in a gene therapy regimen for gene therapy approaches are based on retroviruses, lentiviruses, adenoviruses and adeno-associated viruses.

Adeno-associated viruses (AAVs) are promising candidates for use in clinical practice because they are classified as relatively safe. AAV vectors are able to introduce a transgene into a tissue and express the gene stably and efficiently in the tissue. At the same time, these vectors have no known pathogenic mechanisms [10]. Of particular importance for clinical use are the AAV vectors of serotype 2 (AAV2), which are considered to be particularly well investigated. After the AAV vectors are introduced, the transgenes can be incorporated in different forms in the transfected cells—for example as episomal, single- or double-stranded DNA. Concatamer forms of the DNA have also been demonstrated in transduced cells.

The genome of AAV2 is formed by a linear, single-stranded DNA molecule of approximately 4700 nucleotides in length and has inverted terminal repeats (ITRs) at both ends. The genome also includes two large open reading frames which are called the replication region (rep) and the capsid region (cap). The replication region encodes proteins that are required as part of the virus replication. The capsid region, however, encodes for the structural proteins VP1, VP2 and VP3, which make up the icosahedral capsid of the virus.

Like most vectors which have gene therapy applications and are known in the prior art, however, wild-type AAV vectors, such as the AAV2 vectors described above, do not possess sufficient specificity for a particular tissue, and infect a wide variety of cell types. As such, systemic administration of wild-type vectors leads to insufficient transduction of lung tissue, and severe immune reactions are expected in the treatment subject due to the unwanted transduction of other tissues. Progress in the development of viral vectors which have an increased specificity for particular organs has been made in the past by the use of peptide ligands, which are able to direct the vectors to a particular organ [11-12]. It has been shown that certain peptide ligands bring about a "homing" to various organs such as the brain.

Reading [13] describes a method which enables the screening for tropism-modified capsids of AAV2 in randomized peptide libraries. From these libraries, vectors can be isolated which specifically transduce a desired cell type in vitro. However, it has been surprisingly found that capsids selected in this manner are often unsuitable for use in vivo because they lack the necessary specificity in animal models [14].

There remains a great need for agents that are able to modulate the tropism of viral vectors and thus ensure adequate cell or tissue specificity to enable targeted delivery of a viral vector into the lung. Such vectors enable specific expression of therapeutic genes in lung tissue, for the corresponding, effective treatment of diseases and/or disorders of the lungs.

The present invention makes available viral vectors for targeted gene transfer to the lungs. The viral vectors according to the invention express on their capsid surface a previously unknown amino acid sequence that is specifically recognized in vivo by receptors on the endothelial tissue of the lung. As such, the viral vectors of the present invention specifically transduce the lung tissue of a patient following systemic administration to the same.

The viral vectors according to the invention also enable a strong and persistent expression of a transgene in the endothelial cells of the lung with only minor immune response, and are therefore particularly suitable for gene therapy treatments of certain pulmonary disorders and/or lung diseases. After transfection, the AAV vectors only instigate a minor immune response in the host and are therefore particularly suitable for gene therapy.

DESCRIPTION OF THE INVENTION

In the present invention, various lung-specific sequences were identified by selection in a randomized AAV2 heptamer peptide library. Beginning with the identified peptide sequence ESGHGYF (SEQ ID NO: 2), the recombinant viral vector rAAV2-ESGHGYF (SEQ ID NO:9) was prepared, in which the peptide sequence ESGHGYF (SEQ ID NO: 2) is expressed as a partial sequence of the capsid protein VP1. Subsequently, the vector rAAV2-ESGHGYF (SEQ ID NO:9) was administered intravenously to mice, and a unique specificity of the vector for lung endothelial tissue was observed both in vitro and in vivo. The specificity was demonstrated by staining with CD31, as described in the examples below. Moreover, by replacing the amino acids glutamic acid (E) and serine (S) at the N-terminus of the peptide, it was possible to use an alanine-scan to show that these two amino acids are not relevant for the specificity of the transduction. As such, only the core structure GHGYF (SEQ ID NO: 1) is responsible for the lung specificity.

The present invention therefore provides various lung-specific peptide sequences which are particularly suited for directing therapeutic agents such as viral vectors to the lungs of a subject being treated.

A first aspect of the present invention accordingly relates to a peptide, polypeptide, or protein that binds specifically to endothelial cells in the lungs, wherein the peptide, polypeptide, or protein comprises the amino acid sequence of SEQ ID NO: 1. The peptide, polypeptide, or protein preferably comprises the amino acid sequence of SEQ ID NO: 2 or a variant thereof which differs from the amino acid sequence of SEQ ID NO: 2 by the modification of at least one of the two N-terminal amino acids. The peptide, polypeptide or protein according to the invention preferably binds to endothelial cells of the lung—in particular, the human lung.

In another aspect, the invention relates to a peptide, polypeptide or protein which binds specifically to endothelial cells of the lung, wherein the peptide, polypeptide or protein comprises the amino acid sequence of SEQ ID NO: 3, SEQ ID NO: 4 or SEQ ID NO: 5, In the context of the present disclosure, the term "peptide" refers to a linkage of 2-10 amino acids which are connected to each other by a peptide bond. The term "polypeptide" refers to a linkage of 11-100 amino acids that are connected to each other by a peptide bond. Polypeptides with more than 100 amino acids are referred to herein as a "protein." In a particularly preferred embodiment according to the invention, the lung-specific peptide sequence of SEQ ID NO: 1 or SEQ ID NO: 2, or the variant of SEQ ID NO: 2, according to the invention is a part of a capsid protein of a virus. This means that the lung specific sequence is present as part of a capsid protein of the virus. To produce such capsid proteins, a corresponding nucleotide sequence which codes for the lung-specific peptide is cloned into the region of the virus genome which codes for a capsid protein of the virus. If the lung specific sequence is expressed as part of a capsid protein, it can be presented in many copies across the surface of the viral vector.

The capsid protein is preferably one which is derived from an adeno-associated virus (AAV). The AAV can be any of the serotypes described in the prior art, wherein the capsid protein is preferably derived from an AAV of one of the serotypes 2, 4, 6, 8 and 9. A capsid protein of an AAV of serotype 2 is particularly preferred.

The capsid of the AAV wild-type is made up of the capsid proteins VP1, VP2 and VP3, which are encoded by the overlapping cap region. All three proteins have the same C-terminal region. The capsid of AAV comprises about 60 copies of the proteins VP1, VP2 and VP3, expressed in a ratio of 1:1:8. If a nucleotide sequence coding for one of the lung-specific peptides described herein is cloned at the C-terminus into the reading frame of VP1 (i.e., in the region that is identical in all three proteins), it can be expected that theoretically 60 of the specific peptides can be found on the capsid surface.

If an AAV vector in the context of the present invention is modified, the nucleotide sequence coding for the lung-specific peptide is then cloned into the cap region at the 3' end of the genome. The gene encoding the lung-specific peptide sequence can be cloned into the genomic sequence of one of the capsid proteins VP1, VP2 or VP3. The capsid proteins of AAV2 are illustrated by way of example in SEQ ID NO: 6 (VP1), SEQ ID NO: 7 (VP2), and SEQ ID NO: 8 (VP3).

In one particularly preferred embodiment according to the invention, the gene encoding the lung-specific peptide sequence is cloned into the reading frame of a VP1 gene, preferably in the VP1 gene of AAV2 shown in SEQ ID NO: 6. It should be noted in this case that the insertion of the cloned sequence does not lead to any change of the reading frame, nor to a premature termination to the translation. The methods required for the above are readily apparent to a person skilled in the art.

In all three capsid proteins of AVV, sites have been identified at which peptide sequences can be inserted for the homing function [15-20]. Among other things, the arginine which occurs in the VP1 of AAV2 at position 588 (R588) has specifically been proposed for the insertion of a peptide ligand [21-22]. This amino acid position of the viral capsid is apparently involved in the binding of AAV2 to its natural receptor. It has been suggested that R588 is one of four arginine residues which mediates the binding of AAV2 to its natural receptor [23-24]. A modification in this region of the capsid weakens the natural tropism of AAV2, or eliminates it completely.

Accordingly, it is particularly preferred according to the invention that the inventive lung specific peptide sequence of SEQ ID NO: 1 or SEQ ID NO: 2 (or their variants), or of one of the lung-specific peptide sequences of SEQ ID NO: 3, SEQ ID NO: 4 or SEQ ID NO: 5, is present in inserted form in the region of the amino acids 550-600 of the VP1 protein of AAV2, in particular the protein of SEQ ID NO: 6.

Even more preferably, the lung-specific peptide sequence is present in inserted form in the region of amino acids 560-600, 570-600, 560-590, 570-590 of the VP1 protein.

Thus, the amino acid sequence of SEQ ID NO: 1 or SEQ ID NO: 2 or their variants (or alternatively, the peptide sequences of SEQ ID NO: 3, SEQ ID NO: 4 or SEQ ID NO: 5), adjoin, by way of example directly behind, one of the following amino acids of the VP1 protein, particularly the protein of SEQ ID NO: 6: 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599 or 600. It is particularly preferred that the amino acid sequence of SEQ ID NO: 1 or SEQ ID NO: 2 or its variants (or alternatively, the peptide sequences of SEQ ID NO: 3, SEQ ID NO: 4 or SEQ ID NO: 5) follows the amino acid 588 of the VP1 protein of SEQ ID NO: 6, as shown in the examples. It is possible in this case that one or more, and particularly up to 5 (for example, 1, 2, 3, 4 or 5) amino acids which are the result of the cloning are situated between the arginine residue at position 588 and the first amino acid of SEQ ID NO: 1 or SEQ ID NO: 2, or the variant of SEQ ID NO: 2. Likewise, one or more, and particularly up to 5 (i.e., 1, 2, 3, 4, or 5) amino acids can be situated behind the last amino acid of SEQ ID NO: 1 or SEQ ID NO: 2, or the variant of SEQ ID NO: 2.

The sites and regions in the amino acid sequence of the capsid protein indicated above for VP1 apply analogously to the capsid proteins VP2 and VP3 of AAV2. Because the three capsid proteins VP1, VP2 and VP3 of AAV2 differ only by the length of the N-terminal sequence and accordingly have an identical C-terminus, a person skilled in the art will have no problem making a sequence comparison to identify the sites indicated above, for the insertion of the peptide ligands, in the amino acid sequences of VP1 and VP2. As such, the amino acid 588 in VP1 corresponds to position R451 of VP2 (SEQ ID NO: 7) and/or position R386 of VP3 (SEQ ID NO: 8).

SEQ ID NO: 9 shows an example of the sequence of the VP1 protein of AAV2 after introduction of the peptide sequence of SEQ ID NO: 2. Due to the cloning, the capsid protein has two additional amino acids which do not occur in the native sequence of the VP1 protein of AAV2. As such, the peptide sequence of SEQ ID NO: 2 is flanked at its N-terminus by a glycine in position 589, and at its C-terminus by an alanine in position 597. In addition, the asparagine at position 587 of the native sequence is replaced with a glutamine.

In one particular embodiment, the present invention therefore also relates to a capsid protein which comprises or consists of:

(a) the amino acid sequence of SEQ ID NO: 9;

(b) an amino acid sequence which is at least 80% identical to the amino acid sequence of SEQ ID NO: 9; or (c) a fragment of one of the amino acid sequences defined in (a) or (b).

In a further aspect, the invention is directed to a viral capsid, which comprises a peptide, polypeptide or protein which specifically binds to cells of the lung, and which has the amino acid sequence of SEQ ID NO: 1 or SEQ ID NO: 2 or a variant of SEQ ID NO: 2 as described above (or alternatively, the peptide sequences of SEQ ID NO: 3, SEQ ID NO: 4 or SEQ ID NO: 5).

Furthermore, the present invention also provides a nucleic acid encoding a peptide, polypeptide or protein as described above. A nucleic acid which encodes a capsid protein which comprises a peptide, polypeptide or protein according to the invention as described above, is likewise provided. Preferably, the nucleic acid coding for the capsid protein comprises the nucleotide sequence of SEQ ID NO: 10 or a nucleotide sequence derived from the same, with at least 80% sequence identity. A plasmid comprising such a nucleic acid is also provided.

In yet another aspect, the invention relates to a recombinant—i.e., produced by means of genetic engineering techniques—viral vector, having a capsid and at least one transgene packaged therein, wherein the capsid comprises at least one capsid protein having the amino acid sequence of SEQ ID NO: 1 or SEQ ID NO: 2, or of a variant of SEQ ID NO: 2 which differs from the amino acid sequence of SEQ ID NO: 2 by modification of at least one of the two N-terminal amino acids. Alternatively, the capsid protein can also comprise the amino acid sequence of SEQ ID NO: 3, SEQ ID NO: 4 or SEQ ID NO: 5. The recombinant viral vector can be a recombinant AAV vector—for example, of serotype 2, 4, 6, 8, 9. AAV vectors of serotype 2 are particularly preferred.

The different AAV serotypes differ mainly by their natural tropism. As such, wild-type AAV2 binds more readily to alveolar cells than to lung epithelial cells, while AAV5, AAV6 and AAV9 are capable of greater transduction of epithelial cells of the respiratory tract. A person skilled in the art can take advantage of these natural differences in the specificity of the cells to further amplify the specificity mediated by the peptides according to the invention for certain cells or tissues. At the nucleic acid level, the various AAV serotypes are highly homologous. For example, serotypes AAV1, AAV2, AAV3 and AAV6 are 82% identical on the nucleic acid level [25]. The capsid of the viral vectors according to the invention comprises one or more transgenes. A gene which has been introduced by genetic engineering into the genome of the vector is termed a transgene. The transgene (or transgenes) can be DNA or RNA. Preferably, it is single-stranded DNA (ssDNA) or double-stranded DNA (dsDNA), such as genomic DNA or cDNA. Preferably, the transgene which is to be transported with the aid of the recombinant viral vector according to the invention is a human gene. Suitable transgenes include, for example, therapeutic genes to replace a dysfunctional gene in patients. They can also be genes which are not expressed in the corresponding target tissue, or are only expressed to an insufficient extent. In one preferred embodiment, the transgene which is expressed from the viral vector according to the invention is a gene encoding a nitric oxide synthase (NOS) or the bone morphogenic protein receptor 2 (BMPR2). In the case of NOS, endothelial NOS (eNOS) or inducible NOS (iNOS) can be encoded. The genes encoding eNOS and iNOS can be used for the treatment of a pulmonary disorder or pulmonary disease in a patient—in particular pulmonary hypertension or pulmonary arterial hypertension.

In a further embodiment, the transgene encodes a radioprotective protein such as a radioprotective enzyme. A major limitation of radiotherapy in the treatment of cancer is the radiation-induced damage to the normal tissue, which often makes a reduction in radiation dose, an interruption of the treatment regimen, or even a complete abandonment of this form of therapy necessary. The lung is a therapeutically particularly relevant site of tumor growth but at the same time a particularly radiosensitive organ, which is why primary tumors there often can only be treated to a limited extent with radiotherapy, and diffuse tumor growth usually cannot be treated at all with radiotherapy. With the help of lung-specific vectors of the present invention, the healthy tissue surrounding the malignant tissue can be protected by targeted expression of radioprotective proteins. In one preferred embodiment, the transgene which is introduced into the healthy lung tissue is a manganese superoxide dismutase (MnSOD) which catalyzes the conversion of superoxide anions—one of the critical factors in radiation-induced toxicity—to hydrogen peroxide. A further embodiment proposed here involves the kinase domains of the ataxia telangiectasia mutant (ATM) gene, which contributes to the repair of DNA damage caused by radiation. In a further preferred embodiment, both genes are introduced by means of the presently described vectors into the patient undergoing treatment.

In a further embodiment, the transgene encodes for human alpha-1-antitrypsin. The lack of sufficient quantities of alpha-1-antitrypsin is the cause of Laurell-Eriksson syndrome, a hereditary metabolic disease which can lead to emphysema or cirrhosis. Alpha-1-antitrypsin is required for the regulation of the activity of proteases in the serum. The lack of this inhibitor leads to increased proteolysis in the serum and accordingly to the severe sequelae named above.

The viral vectors of the present invention are particularly suitable for use in a method for therapeutic treatment of diseases of the lung. Lung disorders in the context of the invention include, in particular, all kinds of vascular diseases of the lung such as pulmonary hypertension, as well as lung tumors, alpha-1-antitrypsin deficiency (A1AD), and others. For example, lung tumors which are suitable for treatment using the vectors according to the invention include small cell lung cancer (SCLC), squamous-cell carcinoma, adenocarcinoma, and large cell lung carcinoma. In one preferred embodiment, the viral vectors of the present invention are used for therapeutic treatment of pulmonary hypertension or pulmonary arterial hypertension.

In yet another embodiment, the transgene encodes an antitumor agent, such as a tumor suppressor protein, or an immunomodulator such as a cytokine (such as interleukin 1 to 4, gamma-interferon, p53), which is intended to be transported selectively to the lung tissue of the patient.

The vectors can also be used to transport antisense-RNA, ribozymes, or the like into the endothelial tissue of the lung. Furthermore, vectors according to the invention can also comprise transgenes encoding secretory proteins that are intended for systemic administration in the bloodstream. Such secretory proteins can be efficiently deposited in the bloodstream via the pulmonary capillary bed, which is part of the cardiovascular system.

As used herein, the term "subject" indicates any human or animal organism that can be infected by AAV vectors. Preferably, the subject being treated is a mammal such as a human, a primate, a mouse or a rat. In one preferred embodiment, the subject to be treated is a human. After transfection into the subject, the vector brings about a site-specific expression of the transgene in the cells of the lung endothelium.

The transgene can be present in the viral vector in the form of an expression cassette, which in addition to the sequence of the transgene to be expressed comprises further elements necessary for expression, such as a suitable promoter which controls the expression of the transgene after infection of the appropriate cells. Suitable promoters include, in addition to the AAV promoters such as the cytomegalovirus (CMV) promoter or the chicken beta actin/cytomegalovirus hybrid promoter (CAG), an endothelial cell-specific promoter such as the VE-cadherin promoter, as well as steroid promoters and metallothionein promoters. In one particularly preferred embodiment, the transgene according to the invention comprises a pulmonary endothelium-specific promoter which is connected by a functional bond to the transgene to be expressed. In this way, the specificity of the vectors according to the invention can be further increased for lung endothelium cells. As used herein, a pulmonary endothelium-specific promoter is a promoter whose activity in lung endothelial cells is at least 2-fold, 5-fold, 10-fold, 20-fold, 50-fold or 100-fold higher than in a cell which is not a pulmonary endothelium cell. Preferably, this promoter is a human promoter. The expression cassette can also include an enhancer element for increasing the expression levels of exogenous protein to be expressed. Furthermore, the expression cassette can include polyadenylation sequences, such as the SV40 polyadenylation sequences or polyadenylation sequences of bovine growth hormone.

The viral vectors according to the invention can, preferably as part of one of their capsid proteins, comprise the amino acid sequence of SEQ ID NO: 1, SEQ ID NO: 2, SEQ ID NO: 3, SEQ ID NO: 4 or SEQ ID NO: 5. Alternatively, variants of the amino acid sequence of SEQ ID NO: 2 can be used, the same differing from the amino acid sequence of SEQ ID NO: 2 by the modification of at least one of the two N-terminal amino acids. The modification can be a substitution, deletion or insertion of amino acids, as long as the variant retains the ability to communicate, as part of the capsid, the specific binding of the vector to the receptor structures of endothelial cells of the lung. The invention therefore also extends to variants of the sequence of SEQ ID NO: 2 in which one of the two N-terminal amino acids of SEQ ID NO: 2 has been changed. These variants, which are within the scope of the invention, therefore have a sequence identity of more than 85% to the amino acid sequence shown in SEQ ID NO: 2 when the sequences are compared using the programs GAP or BESTFIT. These computer programs for determining amino acid sequence identity are sufficiently known in the art.

The variant of the sequence of SEQ ID NO: 2 can be based on the substitution of one or two of the N-terminal amino acids—that is, one or both N-terminal amino acids can be replaced with another amino acid. Preferably, the substitution by which the variants of the amino acid sequence in SEQ ID NO: 2 differ is a conservative substitution—i.e., a substitution of one amino acid by an amino acid of similar polarity which gives the peptide similar functional properties. Preferably, the substituted amino acid is from the same group of amino acids as the amino acids which are replaced. For example, a hydrophobic residue can be replaced with another hydrophobic residue, or a polar residue by another polar residue. Functionally similar amino acids which can be exchanged for each other by a conservative substitution include, for example, non-polar amino acids such as glycine, valine, alanine, isoleucine, leucine, methionine, proline, phenylalanine, and tryptophan. Examples of uncharged polar amino acids are serine, threonine, glutamine, asparagine, tyrosine, and cysteine. Examples of charged, polar (acidic) amino acids include histidine, arginine and lysine. Examples of charged, polar (basic) amino acids include aspartic acid and glutamic acid.

Those amino acid sequences in which an amino acid has been inserted into the region of the two N-terminal amino acids of SEQ ID NO: 2 are also considered variants of the amino acid sequence shown in SEQ ID NO: 2. Such insertions can in principle be carried out as long as the resulting variant retains its ability to bind specifically to endothelial cells of the lung. In addition, in the present context, those proteins in which one of the two N-terminal amino acids of SEQ ID NO: 2 is missing are considered to be variants of the amino acid sequence shown in SEQ ID NO: 2. This requires in turn that the correspondingly deleted variant binds specifically to endothelial cells of the lung.

Also encompassed by the invention are lung endothelium-specific variants of the amino acid sequence shown SEQ ID NO: 2, which are structurally modified at one or both N-terminal amino acids—by way of example by introducing a modified amino acid. According to the invention, these modified amino acids can be amino acids that have been modified by biotinylation, phosphorylation, glycosylation, acetylation, branching and/or cyclization.

Viral vectors with capsids which comprise one of the peptide sequences according to the invention or comprise a variant thereof as defined above bind specifically to endothelial cells of the lung. As used herein, a "specific" binding of the vectors according to the invention means that the vectors accumulate after systemic administration mainly on or in the endothelial cells of the lung. This means that more than 50% of the originally administered vector genomes accumulate in the endothelial cells, or in the area of the endothelial cells, of the lungs, while less than 50% accumulate in other cells or tissues (such as in the spleen or liver), or the area thereof. It is preferred that more than 60%, 70%, 80%, 90%, 95%, or even more than 99% of the originally administered vector genomes accumulate in, or in the region of, the endothelial cells of the lung. Specific binding of the vectors can also be determined via the expression of the transgene. In the case of viral vectors which bind specifically to endothelial cells of the lung, more than 50% of the total expression of the transgene occurs in, or in the region of, the endothelial cells of the lung, while less than 50% of the expression can be observed in, or in the region of, other tissues. It is preferred, however, that more than 60%, 70%, 80%, 90%, 95%, or even more than 99% of the total measured expression of the transgene occurs in, or in the region of, the endothelial cells of the lungs.

A person skilled in the art will easily be able to determine the specific binding of the vectors according to the invention to endothelial cells of the lung and the expression of the transgene introduced using the vectors. Methods for measuring the specificity of transduction and expression, suitable for this purpose, are shown in the examples below.

It is also preferable according to the invention that vectors whose capsids comprise variants of the amino acid sequence shown in SEQ ID NO: 2 have at least about 50% of the binding activity of a corresponding viral vector with a capsid which has the amino acid sequence shown in SEQ ID NO: 2. It is even more preferred that the variants have about 60%, 70%, 80%, 90%, 95%, 96%, 97%, 98%, or 99% of the binding activity of a corresponding viral vector whose capsid has the amino acid sequence shown in SEQ ID NO: 2. The binding activity of the vectors can be measured with the aid of in vitro assays, as described in the included examples.

Preferably, the binding activity of the vectors according to the invention, as can be determined by distribution of the vector genomes or expression of the transgene, for endothelial cells of the lung is at least 2-fold, 5-fold, 10-fold, 20-fold, 50-fold, 75-fold, 100-fold, 150-fold, 200-fold, 250-fold, 500-fold, 600-fold, 700-fold, 800-fold, 900-fold, 1000-fold, 2000 fold, 5000-fold, or 10,000-fold higher than the binding activity for a control cell which is not a lung endothelium cell (such as a spleen or liver cell).

The invention also relates to a cell that comprises a peptide, polypeptide or protein according to the invention, a nucleic acid encoding the same, a plasmid comprising such a nucleic acid, or a recombinant AAV vector as described above. It is preferably a human cell or cell line.

In one embodiment, a cell has been, for example, obtained from a human subject by biopsy and then transfected with the viral vector in an ex vivo procedure. The cell can then be re-implanted in the subject, or be supplied in other ways to the subject—for example by transplantation or infusion. The likelihood of rejection of transplanted cells is lower when the subject from which the cell was derived is genetically similar to the subject to which the cell is administered. Preferably, therefore, the subject to whom the transfected cells are supplied is the same subject from which the cells were previously obtained. The cell is preferably a human lung cell, particularly a cell of the human pulmonary endothelium. The cell to be transfected can also be a stem cell, such as a human adult stem cell. It is particularly preferred according to the invention that the cells to be transfected are autologous cells that have been transfected ex vivo with the viral vector according to the invention, for example the recombinant AAV2 vector described above. The cells are preferably used in a method for treating a pulmonary disorder or a lung disease in a subject.

In another aspect, the invention relates to a method for producing an AAV vector in which a plasmid is used which encodes a capsid protein, the same comprising the amino acid sequence of SEQ ID NO: 1 or SEQ ID NO: 2, or a variant thereof. Alternatively, the vector can also comprise the amino acid sequence of SEQ ID NO: 3, SEQ ID NO: 4 or SEQ ID NO: 5. The basic method of producing recombinant AAV vectors comprising a transgene to be expressed is described in the prior art sufficiently [28]. HEK 293-T cells are transfected with three plasmids. A first plasmid comprises the cap and rep regions of the AAV genome, but the naturally occurring inverted repeats (ITRs) are missing. The cap region of this plasmid comprises a gene encoding at least one modified capsid protein, i.e., a gene which comprises the peptide sequence according to the invention. A second plasmid comprises a transgene expression cassette which is flanked by the corresponding ITRs, which constitute the packaging signal. The expression cassette is therefore packaged into the capsid in the course of the assembly of the viral particles. The third plasmid is an adenoviral helper plasmid, on which are encoded the helper proteins E1A, E1B, E2A, E4orf6, VA, which are required for AAV replication in the HEK 293-T cells.

Conditions which allow the accumulation and purification of the recombinant vectors according to the invention are known in the art. The vectors according to the invention can be purified, for example, by gel filtration processes—for example using a Sepharose—desalinated, and subsequently purified by filtration. Other purification methods can further comprise a cesium chloride or iodixanol gradient ultracentrifugation process. Purification reduces potentially detrimental effects in the subject to which the adeno-associated viral vectors are administered. The administered virus is substantially free of wild-type and replication-competent virus. The purity of the virus can be checked by suitable methods such as PCR amplification.

In a further aspect, the invention provides a pharmaceutical composition comprising a viral vector of the present invention, particularly an AAV vector. The viral vector in this case is administered in a therapeutically effective amount to the patient, i.e., in an amount sufficient to considerably improve at least one symptom of the lung dysfunction or lung disease being treated, or to prevent the progression of the disease. Symptoms that are regularly associated with a lung disease include cough, fever, chest pain, hoarseness and difficulty breathing. A therapeutically effective amount of the vector according to the invention causes a positive change in one of the mentioned symptoms, i.e., a change which results in the phenotype of the affected subject approximating the phenotype of a healthy subject who does not suffer from a pulmonary disease.

In one preferred embodiment according to the invention, the administration of the viral vector occurs in an amount which leads to a complete or substantially complete healing of the lung dysfunction or lung disease. The pharmaceutical composition accordingly comprises a therapeutically effective dose of the vector according to the invention. A therapeutically effective dose will generally be non-toxic for the subject who undergoes the treatment.

The exact amount of viral vector which must be administered to achieve a therapeutic effect depends on several parameters. Factors that are relevant to the amount of viral vector to be administered are, for example, the route of administration of the viral vector, the nature and severity of the lung disease, the disease history of the patient being treated, and the age, weight, height, and health of the patient to be treated. Furthermore, the expression level of the transgene which is required to achieve a therapeutic effect, the immune response of the patient, as well as the stability of the gene product are relevant for the amount to be administered. A therapeutically effective amount of the viral vector can be determined by a person skilled in the art on the basis of general knowledge and the present disclosure.

The viral vector is preferably administered in an amount corresponding to a dose of virus in the range of $1.0 \times 10^{10}$ to $1.0 \times 10^{14}$ vg/kg (virus genomes per kg body weight), although a range of $1.0 \times 10^{11}$ to $1.0 \times 10^{13}$ vg/kg is more preferred, and a range of $5.0 \times 10^{11}$ to $5.0 \times 10^{12}$ vg/kg is still more preferred, and a range of $1.0 \times 10^{12}$ to $5.0 \times 10^{12}$ is still more preferred. A virus dose of approximately $2.5 \times 10^{12}$ vg/kg is most preferred.

The amount of the viral vector to be administered, such as the AAV2 vector according to the invention, for example, can be adjusted according to the strength of the expression of one or more transgenes.

The viral vector of the present invention, such as the preferred AAV2 vector according to the invention, for example, can be formulated for various routes of administration—for example, for oral administration as a capsule, a liquid or the like. However, it is preferred that the viral vector is administered parenterally, preferably by intravenous injection or intravenous infusion. The administration can be, for example, by intravenous infusion, for example within 60 minutes, within 30 minutes or within 15 minutes. It is further preferred that the viral vector is administered locally by injection to the lung during a surgery. Compositions which are suitable for administration by injection and/or infusion typically include solutions and dispersions, and powders from which corresponding solutions and dispersions can be prepared. Such compositions will comprise the viral vector and at least one suitable pharmaceutically acceptable carrier. Suitable pharmaceutically acceptable carriers for intravenous administration include bacteriostatic water, Ringer's solution, physiological saline, phosphate buffered saline (PBS) and Cremophor EL™. Sterile compositions for the injection and/or infusion can be prepared by introducing the viral vector in the required amount into an appropriate carrier, and then sterilizing by filtration. Compositions for administration by injection or infusion should remain stable under storage conditions after their preparation over an extended period of time. The compositions can contain a preservative for this purpose. Suitable preservatives include chlorobutanol, phenol, ascorbic acid and thimerosal. The preparation of corresponding formulations and suitable adjuvants is described, for example, in "Remington: The Science and Practice of Pharmacy," Lippincott Williams & Wilkins; 21st edition (2005).

In a further aspect, the invention relates to a method for the therapeutic treatment of a pulmonary disorder or a pulmonary disease, wherein a viral vector according to the invention, preferably an AAV vector as described above, is administered to a subject. The vector comprises a capsid which has at least one capsid protein having the amino acid sequence of SEQ ID NO: 1 or SEQ ID NO: 2, or a variant as described above of SEQ ID NO: 2. Alternatively, the vector can also comprise the amino acid sequence of SEQ ID NO: 3, SEQ ID NO: 4 or SEQ ID NO: 5. The viral vector further comprises a transgene, for example a therapeutic gene, which is useful for the treatment of the pulmonary disorder or the lung disease. After administration to the subject being treated, preferably by systemic administration such as intravenous injection or infusion, for example, the vector brings about the specific expression of the gene in the endothelial cells of the lung.

BRIEF DESCRIPTION OF THE FIGURES

FIG. 2 shows the sequences of the lung-specific peptides identified by means of the selection method. After the fourth round of selection, a total of four different sequences were identified.

EXAMPLES

All data was determined as mean values±standard deviation (SD). The statistical analysis was performed using the GraphPad Prism 3.0 program (GraphPad Software, San Diego, USA). Data was analyzed by one-way ANOVA followed by multiple comparison tests as per Bonferroni. P values >0.05 were considered significant.

Example 1: Selection of AAV2 Peptide Libraries

For the selection of tissue-specific AAV2 capsids, a random-display peptide library was prepared and selected in four rounds. A random $X_7$-AAV peptide library with a theoretical diversity of $1\times10^8$ individually occurring clones was prepared using a two-stage protocol as previously described [26-27]. A degenerate oligonucleotide was first produced which codes for seven randomized amino acids at nucleotide position 3967 in the AAV genome, which corresponds to the amino acid position R588 in VP1. The oligonucleotide had the sequence: 5'-CAGTCGGCCAGA-GAGGC(NNK)$_7$GCCCAGGCGGCTGACGAG-3' (SEQ ID NO: 11). The second strand was produced using a Sequenase (Amersham, Freiburg, Germany) and the primer with the sequence 5'-CTCGTCAGCCGCCTGG-3' (SEQ ID NO: 12). The double-stranded insert was cut with BglI, purified with the QIAquick Nucleotide Removal Kit (Qiagen, Hilden, Germany) and ligated into the library with SfiI digested library plasmid pMT187-0-3 [26]. The diversity of the plasmid library was determined by the number of clones grown from a representative aliquot of transformed, electrocompetent DH5α bacteria on agar containing 150 mg/ml ampicillin. Library plasmids were harvested and purified by using the Plasmid Preparation Kit from Qiagen. The AAV library genomes were packaged into chimeric wild-type and library AAV capsids (AAV transfer shuttle) by transfecting $2\times10^8$ 293T cells in 10 cell culture dishes (15 cm) with the plasmid pVP3 cm (containing the wild-type cap genes with modified codon usage without the inverted terminal repeats) [27], the library plasmids and the pXX6 helper plasmid [28], wherein the ratio between the plasmids was 1:1:2. The resulting AAV library transfer shuttles were used to infect $2\times10^8$ 293T cells in cell culture dishes (15 cm) with an MOI of 0.5 replication units per cell. Cells were superinfected with Ad5 (provided by the Laboratoire de Therapie Génique, France), with an MOI of 5 plaque-forming units (pfu/cell). The final AAV display library was harvested from the supernatants after 48 hours. The supernatants were concentrated using VivaSpin columns (Viva Science, Hannover, Germany) and purified by iodixanol density gradient ultracentrifugation as previously described [29], and titrated by real-time PCR using the cap-specific primers 5'-GCAG-TATGGTTCTGTATCTACCAACC-3' (SEQ ID NO: 13) and 5'-GCCTGGAAGAACGCCTTGTGTG-3' (SEQ ID NO: 14) with the LightCycler system (Roche Diagnostics, Mannheim, Germany).

Figure 1:
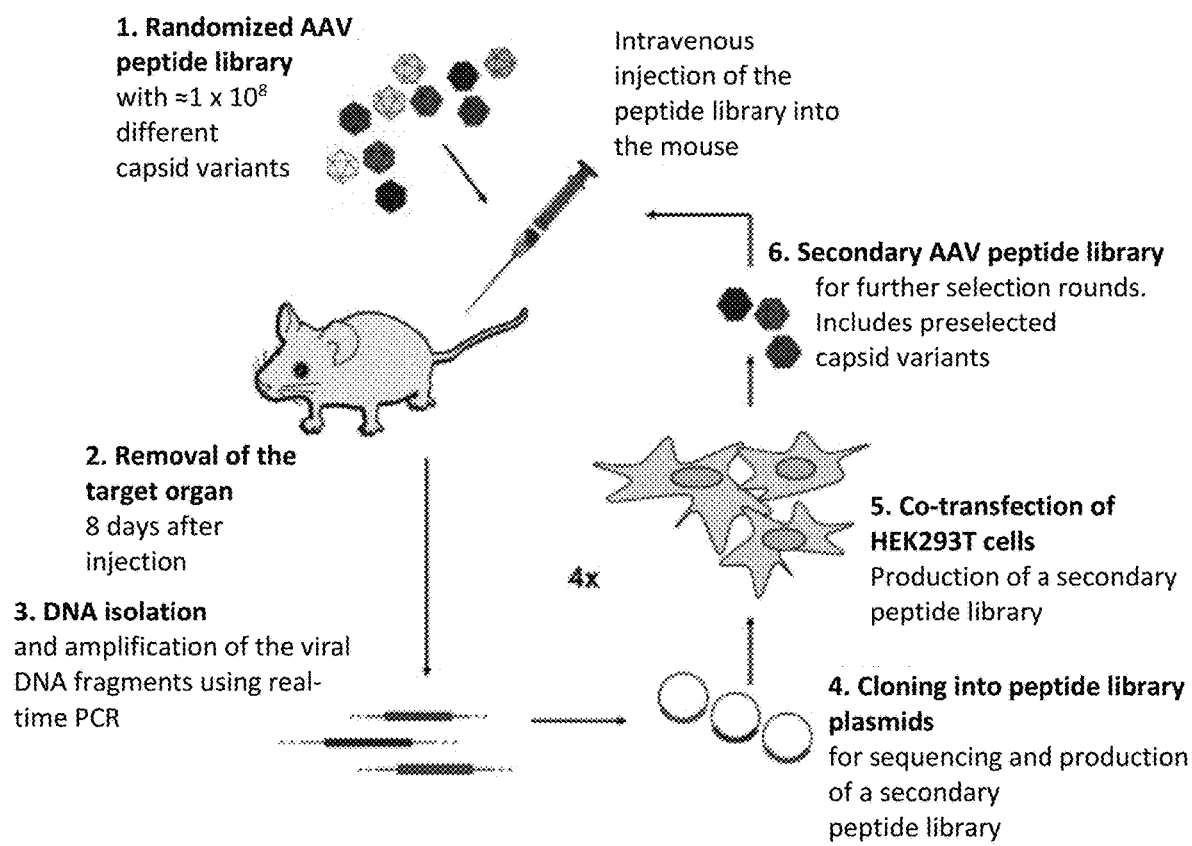
FIG. 1 shows the in vivo selection method of the AAV-peptide library used according to the invention.

For the in vivo biopanning $1\times10^{11}$ particles of the genomic library were injected into the tail vein of FVB/N mice. The particles were given 8 days for the distribution and the infection of the target cells. After 8 days, the mice were killed and the lungs were removed. The total DNA of the tissue was extracted using the DNeasy Tissue Kit (Qiagen). The random oligonucleotides that were included in AAV particles of the library and had accumulated in the tissue of interest were amplified by nested PCR using the primers 5'-ATGGCAAGCCACAAGGACGATG-3' (SEQ ID NO: 15) and 5'-CGTGGAGTACTGTGTGATGAAG-3' (SEQ ID NO: 16) for the first PCR and the primers 5'-GGT-TCTCATCTTTGGGAAGCAAG-3' (SEQ ID NO: 17) and 5-TGATGAGAATCTGTGGAGGAG-3' (SEQ ID NO: 18) for the second PCR. The PCR-amplified oligonucleotides were used to prepare secondary libraries for three additional rounds of selection. The secondary libraries were generated like the primary libraries (see above), but without the additional step of producing transfer shuttles. The secondary plasmid library was used to transfect $2\times10^8$ 293T cells in cell culture dishes (15 cm) at a ratio of 25 library plasmids per cell, wherein the transfection reagent Polyfect (Qiagen) was used. After each round of selection, several clones were sequenced. The applied selection method is shown in FIG. 1.

Results:

After four rounds of selection, a total of 9 clones were sequenced. The sequencing revealed that 5 clones had the peptide sequence ESGHGYF (SEQ ID NO: 2). Other clones showed the peptide sequences ADGVMWL (SEQ ID NO: 3), GEVYVSF (SEQ ID NO: 4) and NNVRTSE (SEQ ID NO: 5). Three of the four peptide sequences, including the dominant clone ESGHGYF(SEQ ID NO: 2), as well as ADGVMWL(SEQ ID NO: 3) and GEVYVSF(SEQ ID NO: 4), displayed at least one hydrophobic aromatic group. The peptides obtained in the various rounds of selection are shown in FIG. 2.

Example 2: Preparation and Quantification of Recombinant AAV Vectors

The clones enriched in Example 1 were produced as recombinant AAV vectors and tested for their transduction profile. Recombinant AAV vectors were produced by triple transfection of HEK293T cells. The cells were incubated at 37° C., 5% $CO_2$ in Dulbecco's modified Eagle Medium (Invitrogen, Carlsbad, USA), supplemented with 1% penicillin/streptomycin and 10% fetal calf serum. Plasmid DNA was transfected into 293T cells with the transfection agent Polyfect (Qiagen, Hilden, Germany). Four days after transfection, the cells were harvested and lysed, and the vectors were purified by means of iodixanol density gradient ultracentrifugation as previously described [29]. For the transfections, pXX6 was used as adenoviral helper plasmid [28], which encodes the luciferase gene pUF2-CMV-luc [27] or the GFP gene pTR-CMV-GFP [30], as was a plasmid encoding the AAV capsid of interest. The plasmids encoding the AAV capsid mutants which had been previously selected from the AAV library, and wild-type controls, were modified pXX2-187 [31] or pXX2 [28]. In addition, for an alanine scanning, further oligonucleotide inserts were made which encode modified variants of the peptide ESGHGYF (SEQ ID NO: 2). The inserts were processed as described into library inserts (see above). To quantify the recombinant vectors, the genomic titer was determined by the LightCycler system, as previously described [32], by real-time PCR using the CMV-specific primers 5'-GGCGGAGTTGTTAC-GACAT-3' (SEQ ID NO: 19) and 5'-GGGACTTTC-CCTACTTGGCA-3' (SEQ ID NO: 20).

Example 3: Examination of the Tropism of the Recombinant AAV Vectors In Vivo

To be able to examine the tropism of the enriched peptides in vivo, the peptides were introduced into the capsid of a recombinant vector comprising a luciferase reporter gene. Vectors with mutated capsids were injected into mice along with control vectors. The AAV vectors were administered intravenously at a dose of $5 \times 10^{10}$ vector genomes (vg)/mouse (n=3 animals per injected AAV clone). On day 14, the animals were anesthetized with isoflurane. The luciferase expression was analyzed using a Xenogen IVIS200 Imaging System (Caliper Lifescience, Hopkinton, USA) with the Living Image 4.0 (Caliper) software, following intraperitoneal injection of 200 µl of luciferin substrate (150 mg/kg, Xenogen) per mouse. Representative, in vivo bioluminescence images of the expression of the transgene at different positions (ventral, dorsal, lateral) were taken when the luminescence in relative light units (photons/sec/cm2) reached the highest intensity. Then the animals were sacrificed, the organs of interest were removed quickly, and images of the expression of the transgene in individual organs were immediately taken. The organs were then frozen in liquid nitrogen and stored at −80° C. Three-dimensional reconstructions of the in vivo luminescence images were obtained by using the DLIT option of the Living Image 4 software, and the emitted light was measured in 5 different wavelengths from 560-640 nm for three minutes each. To quantify the luciferase expression, the organs were homogenized in reporter lysis buffer (RLB, Promega, Madison, USA). The determination of the luciferase reporter gene activity was carried out in a luminometer (Mithras LB9 40, Berthold Technologies, Bad Wildbad, Germany) at 10-second intervals after the addition of 100 µL luciferase assay reagent (LAR, Promega), with a 2-second delay between each of the measurements. The values were normalized in each sample with respect to the total amount of protein using the Roti NanoQuant protein assay (Roth, Karlsruhe, Germany).

Figure 3:
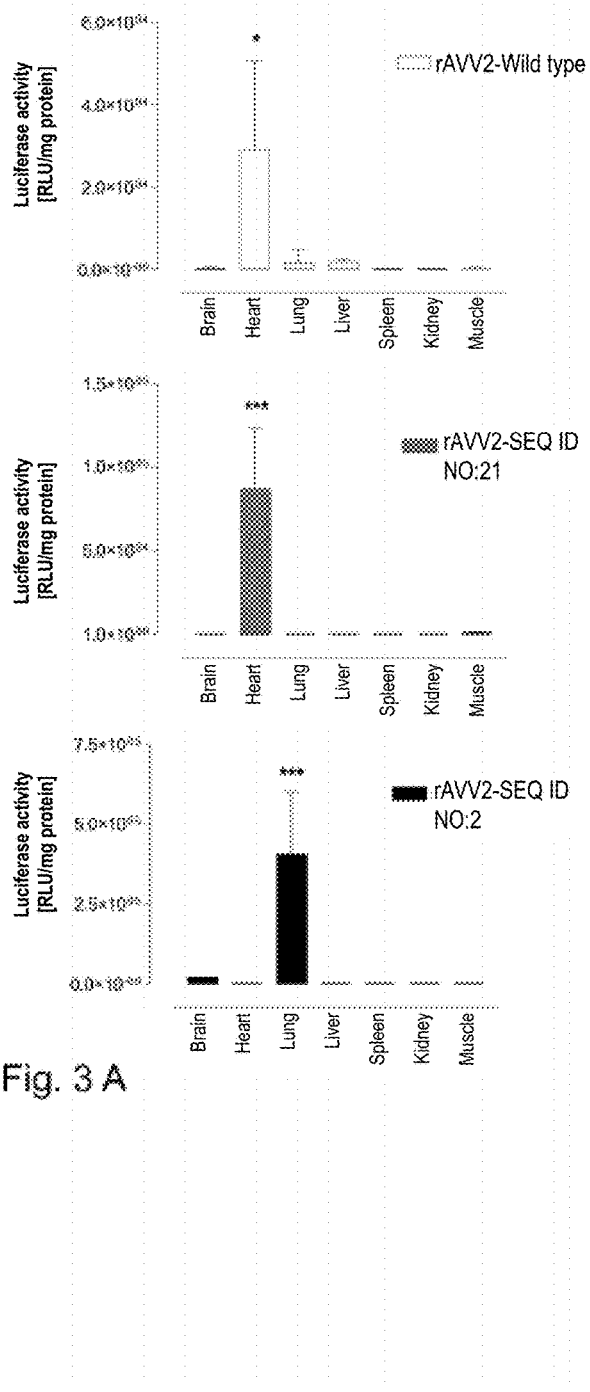
FIG. 3 shows the measurement of the expression of luciferase 14 days after systemic administration of recombinant AAV vectors in mouse organ lysates. A: wild-type AAV2 vector (upper panel) and the insertion control AAV2-CVGSPCG (SEQ ID NO:21, middle panel) induce mainly heart-specific expression. AAV2-ESGHYGF (SEQ ID NO:9, lower panel) induces a strong expression of luciferase, which is simultaneously lung-specific. B: Comparison of the expression levels of wild-type AAV2, AAV2-CVGSPCG (SEQ ID NO:21) and AAV2-ESGHYGF (SEQ ID NO:9) vectors in the heart (upper panel), liver (middle panel) and lung (lower panel). AAV2-ESGHYGF (SEQ ID NO:9) has a greatly attenuated induction of expression in the heart and liver and a significant increase in expression of luciferase in the lung. Mean values are shown with their standard deviation. One-Way ANOVA. $p<0.05=*$; $p<0.01=$; $p<0.001=*$ for n=3.
Figure 3:
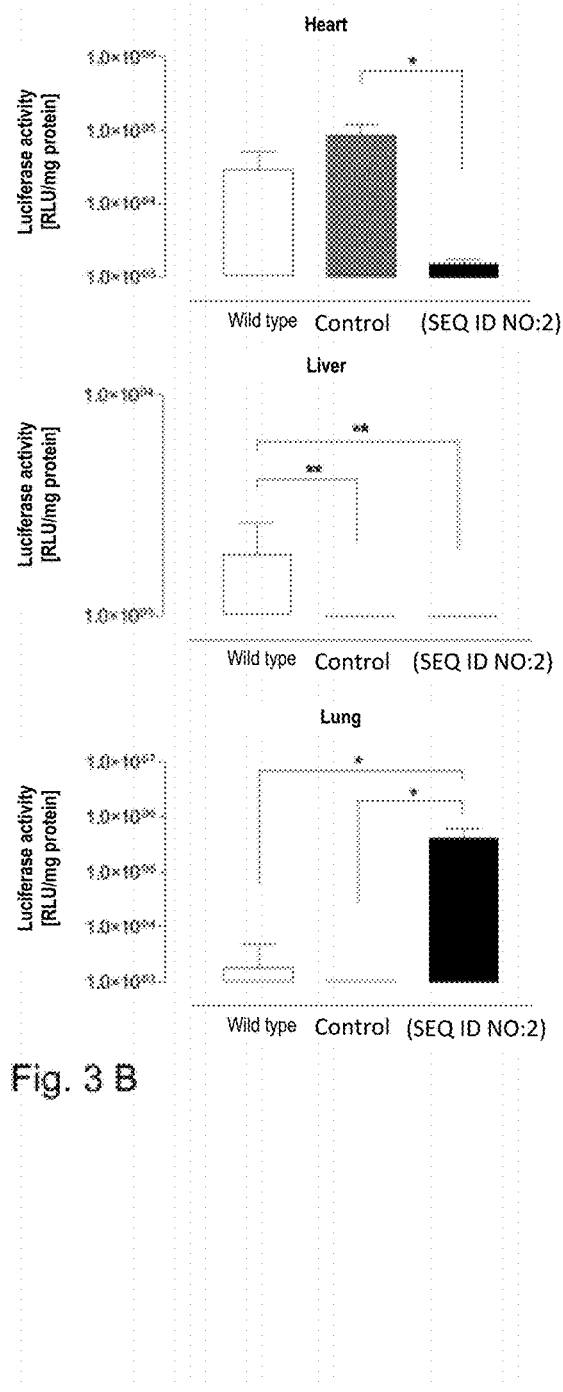

Results:

It was found that the yield with respect to the vector titers for recombinant vectors with luciferase reporter gene was comparable to vectors carrying a wild-type AAV2 capsid, which suggested that the enriched peptides do not adversely affect the assembly of the capsid or packaging of the gene. The in vivo measurement of bioluminescence after 14 days showed that the peptide ESGHGYF (SEQ ID NO: 2) led to a strong and lung-specific expression of the transgene ($\leq 10^5$ p/sec/cm²/r). These results were confirmed by the control experiments carried out ex vivo with explanted organs. A randomly selected control clone of the non-selected library (CVGSPCG, SEQ ID NO:21) led to a weak gene expression that occurred primarily in the heart and in some parts of the abdomen, but not in the lung. Wild-type AAV2 caused a weak gene expression in the heart, liver and skeletal muscle, but not in the lungs. A three-dimensional reconstruction of bioluminescence images confirmed the lung-specific expression. The peptide ADGVMWL (SEQ ID NO: 3), which was also enriched during the in vivo selection, also led to a lung-specific expression of the transgene, but was weaker than for the peptide ESGHGYF(SEQ ID NO: 2). While the gene expression within 14 days after administration of the ADGVMWL (SEQ ID NO:3) luciferase vector was very low, it increased to about $5 \times 10^4$ p/sec/cm²/r and could be observed specifically in the lung 28 days after vector injection. These results were confirmed by the control experiments carried out ex vivo with explanted organs. The investigation of the luciferase activity of tissue lysates from representative organs showed that wild-type AAV2 caused a low gene expression in the heart ($2.9 \times 10^4$ RLU/mg protein, see FIG. 3A, upper panel) and even lower levels of expression in other organs. The control peptide CVSGPCG (SEQ ID NO:21) produced a moderate gene expression in the heart ($8.7 \times 10^4$ RLU/mg protein, see FIG. 3A, middle panel). In contrast, vectors which had the lung specific ESGHGYF (SEQ ID NO:2) capsid led to a strong and specific gene expression in the lung ($4.1 \times 10^5$ RLU/mg protein, see FIG. 3A, lower panel). In the heart and in the liver (i.e., in the two organs in which wild-type AAV2 and the peptide vector CVGSPCG lead to a strong expression), the lung-specific ESGHGYF (SEQ ID NO:2) vectors showed only an expression on the order of the background signal (about $1 \times 10^3$ RLU/mg protein). In contrast, the expression of the transgene in the lungs for the ESGHGYF (SEQ ID NO:2) vectors was more than 200-fold higher than the expression mediated by wild-type AAV2 or by the CVGSPCG (SEQ ID NO:21) control vectors (see FIG. 3B).

Figure 4:
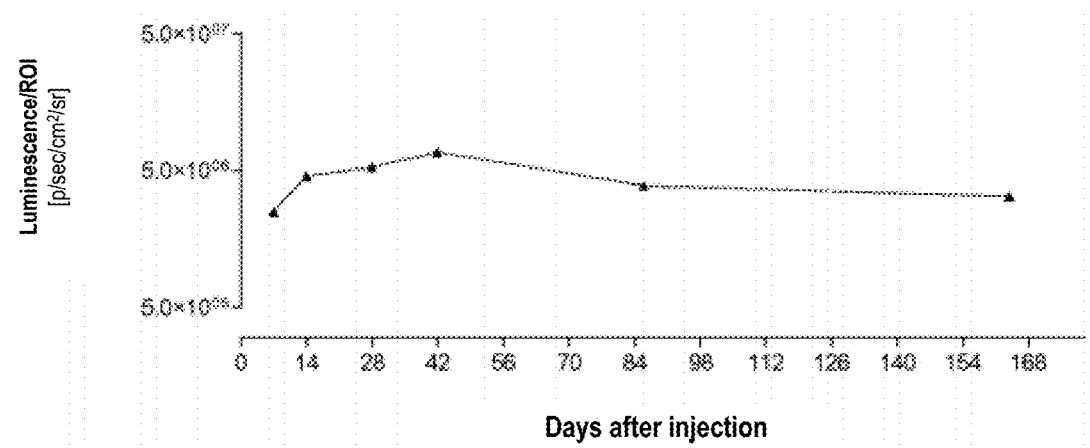
FIG. 4 shows a long-term expression analysis in mouse after systemic administration of recombinant AAV2-ESGHYGF (SEQ ID NO:9) vector. Repeated measurements using the IVIS® 200 Imaging System exhibit stable gene expression in the lung over a period of 168 days (n=1).

The results further showed that the lung-specific expression of the transgene mediated by the ESGHGYF (SEQ ID NO:2) vectors remained organ-specific over a long period. After intravenous administration of the lung-specific AAV2 ESGHGYF (SEQ ID NO:2) luciferase vectors, the expression of the transgene was measured over a period of 164 days. The radiation emitted in the lung region was determined quantitatively. Over the entire period of time, the expression of the transgene was stable at a high level, and was limited to the lung. The lowest expression in the lung was measured at day 7, a peak was reached on day 42, and the radiation declined only slowly to the last measurement on day 164 (FIG. 4).

Example 4: Alanine Scanning for the Peptide ESGHGYF (SEQ ID NO: 2)

To investigate the importance of the individual amino acids in the peptide ESGHGYF (SEQ ID NO:2) in relation to the lung specificity, an alanine scanning was performed.

Results:

It was found that the lung-specific tropism was not changed by replacing the first two amino acids. However, if amino acids 3-4 or 5-7 were exchanged, there was either a total loss of infectivity (position 3 or 4) or a change in specificity to heart or skeletal muscle (positions 5-7).

Example 5: Analysis of the Vector Distribution

In order to check whether the lung-specific expression of the transgene of intravenously injected ESGHGYF (SEQ ID NO:2) vectors is based on a lung-specific homing, first the distribution of vectors was investigated four hours after intravenous administration of $5 \times 10^{10}$ gp/mouse. The quantification of the vector genomes was performed by real-time PCR. First, the total DNA was extracted from the organ concerned at various time points after intravenous administration of $5 \times 10^{10}$ vg/mouse using a tissue homogenizer (Precellys 24, Peqlab, Erlangen, Germany) and the DNeasy Tissue Kit (Qiagen, Hilden, Germany) according to the manufacturer's instructions. The DNA was quantified using a spectrophotometer (NanoDrop ND-2000C, Peqlab). The analysis of the AAV vector DNA in the tissues was performed by quantitative real-time PCR using the above-described CMV-specific primer, wherein 40 ng of template were used, normalized with respect to the total DNA.

Figure 5A:
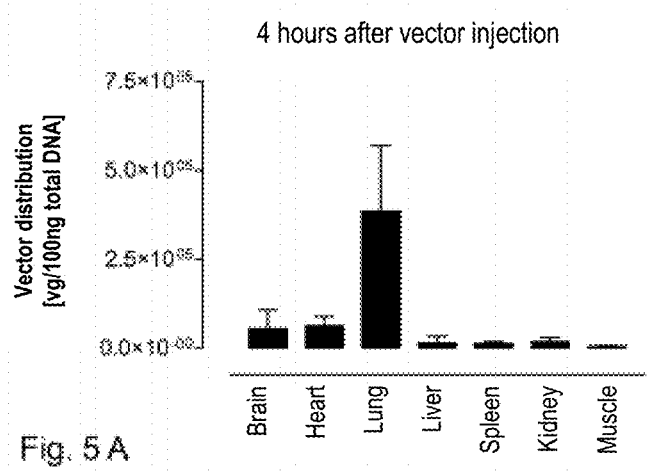
FIG. 5 shows the distribution of recombinant AAV vectors after systemic administration of $5 \times 10^{10}$ gp/mouse by quantitative real-time PCR. A: Distribution of AAV2-ESGHYGF (SEQ ID NO:9) 4 hours after vector administration in seven different organs. B: Distribution of genomes provided by the wild-type AAV2 vector (upper panel), the control vector AAV2-CVGSPCG (SEQ ID NO:21, middle panel) and AAV2-ESGHYGF (SEQ ID NO:9) lower panel). The control vector and wild-type vector accumulate in the reticuloendothelial system of the liver and spleen. AAV2-ESGHYGF accumulates exclusively in the lungs. B: Comparison of the distribution of wild-type AAV2, control vector AAV2-CVGSPCG (SEQ ID NO:21) and AAV2-ESGHYGF (SEQ ID NO:9) in liver (upper panel), spleen (middle panel) and lung (lower panel). Mean values are shown with their standard deviation. One-Way ANOVA. p<0.05=*; p<0.01=; p<0.001=* for n=3.
Figure 5:
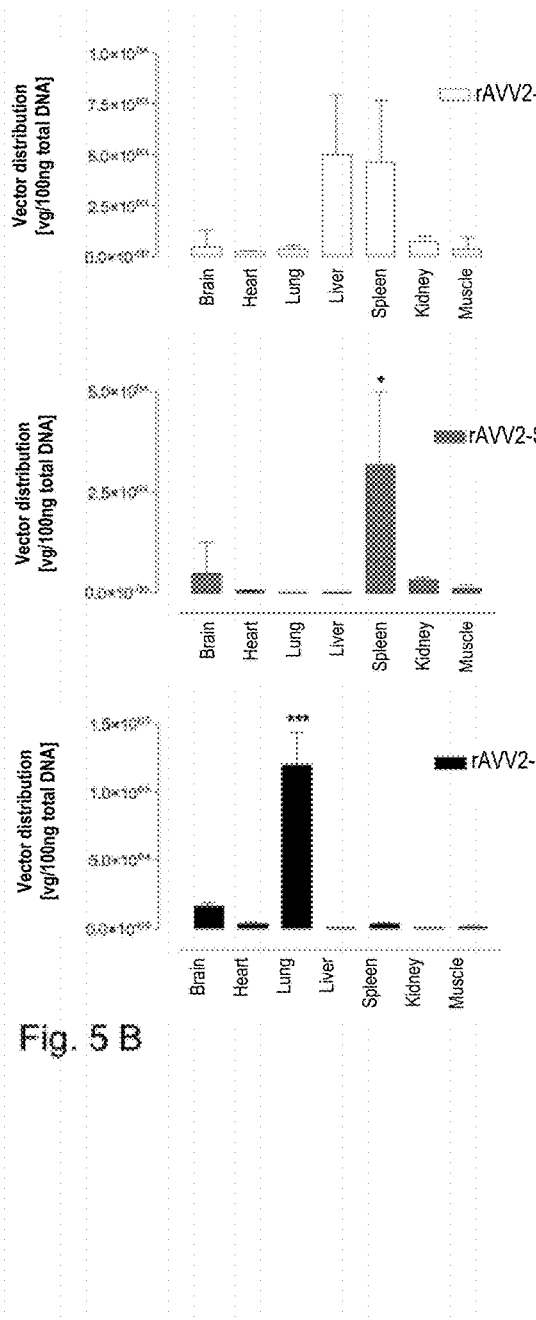
Figure 5:
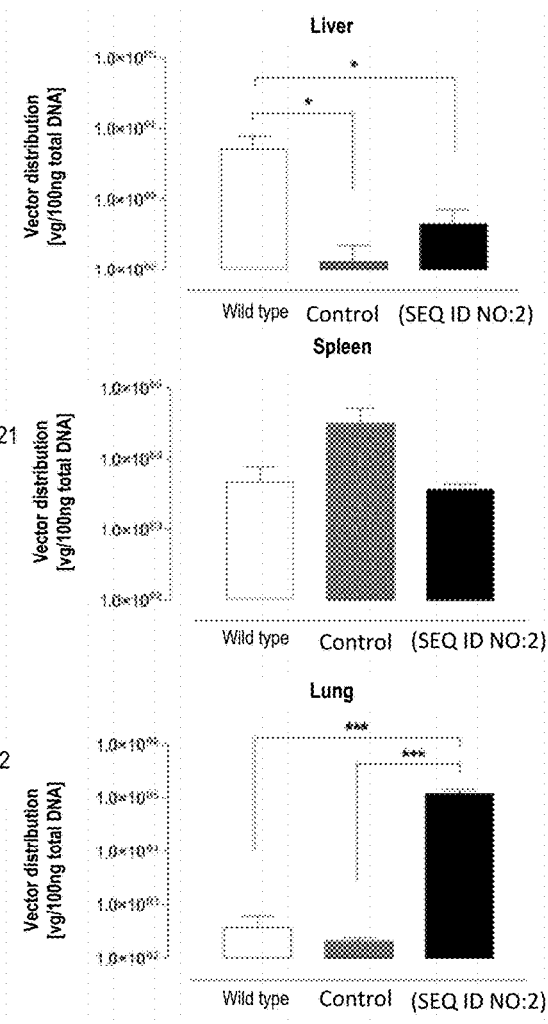

Results:

The quantification of the vector genomes by real-time PCR showed a lung-specific homing of ESGHGYF (SEQ ID NO:2). The amount of vector genomes which could be detected in the lungs ($3.8 \times 10^5 \pm 1.9 \times 10^5$ vg/100 ng total DNA) was about 6-100 times higher than the amount of vector genomes which was demonstrated in another organ (FIG. 5A). To determine the direct correlation between vector homing and expression of the transgene, the vector distribution of wild-type AAV2, the control peptide CVG-SPCG and the lung-specific peptide ESGHGYF (SEQ ID NO:2) was measured 14 days after intravenous administration of $5\times10^{10}$ gp/mouse, i.e., at the time when the expression of the transgene was determined (see above). The genomes provided by wild-type AAV2 vectors were mainly recovered from the liver and spleen, and the genomes of vectors which had the control peptide were obtained largely from the spleen. In total, the amount of vector genomes which were detected in the spleen were relatively equal ($4\times10^3$ vp/100 ng of total DNA) in all examined capsid variants, suggesting a nonspecific capture mechanism for the particles in the reticuloendothelial system which is independent of the provision and the expression of the transgene. In contrast, the distribution data of genomes which were provided by vectors which had the lung-specific peptide ESGHGYF (SEQ ID NO:2) was highly similar to the expression data of the transgene, with a highly specific accumulation observed in the lungs. The amount of vectors detected in the lung which showed the peptide ESGHGYF (SEQ ID NO: 2) was about 250-fold higher than in other organs, and up to 500-fold higher than in lungs which were injected with a wild-type vector or a control capsid vector (FIG. 5B). The same distribution values between the organs were found 28 days after vector administration. The direct comparison between the three vector capsid variants for the quantities of genomes found is shown in FIG. 5C for the three tissues in which relevant amounts of vector DNA were detected. Overall, this data indicates that a lung-specific expression of the transgene, mediated by ESGHGYF (SEQ ID NO: 2) vectors, is achieved by a tissue-specific homing of circulating particles.

Example 6: Immunohistochemistry and Histology

Immunohistochemistry was used to visualize the expression of the transgene at the cellular level in the lung, as well as in a control organ, 14 days after the intravenous administration of the rAAV-GFP vector having the peptide ESGHGYF (SEQ ID NO:2) and/or the wild-type AAV capsid as control. The lungs of the animals were fixed ex situ with 4% (w/v) paraformaldehyde via the trachea under hydrostatic pressure of 20 cm of water for 20 minutes, followed by 24 hours of immersion in the same fixative. The lung tissues were embedded in paraffin. Sections with a thickness of 2 μm were removed from wax, rehydrated and used for immunohistochemistry. An immunohistochemical procedure was performed using polyclonal antibodies for GFP (A-11122, Invitrogen) or CD31 (AB28364, Abcam, Cambridge, USA). Endogenous peroxidase was inactivated with 1% $H_2O_2$ in methanol for 30 minutes. Prior to staining with CD31, the sections were heated in citrate buffer (pH 6.0) for 20 minutes at 100° C. After washing in PBS, the sections were incubated for 30 minutes with PBS, 10% goat serum (Vector Lab, Burlingame, USA) and 2% milk powder (Roth). Primary antibodies were allowed to bind for 1 hour at 37° C. After washing in PBS, the sections were incubated for 30 minutes with a secondary, biotinylated goat anti-rabbit antibody (Vector Lab). Bound antibodies were visualized by using the VECTASTAIN-Elite ABC kit (Vector Lab) and 3,3'-diaminobenzidene (DAB, Sigma-Aldrich, St. Louis, USA). Selected sections were counterstained with Hemalum.

Results:

In the lungs of mice injected with rAAV-ESGHGYF (SEQ ID NO:9), a microscopic examination showed intensive staining of the endothelial cells over the entire pulmonary micro-vasculature and to a slightly lesser extent in the large pulmonary vessels (data not shown). In contrast, pulmonary tissue of mice which was injected with wild-type AAV2 vector showed no staining. To confirm the tissue specificity, the liver was analyzed as a control organ (a tissue which is known to frequently demonstrate high expression of a transgene) after injection of wild-type AAV2 vector. In the liver, hepatocyte staining was observed after administration of wild-type rAAV2 vector; but no staining was observed after administration of rAAV2-ESGHGYF (SEQ ID NO:9) vector. The endothelial lineage of pulmonary cells transduced with the vectors was confirmed by CD31 staining, wherein the pattern obtained by the GFP staining was confirmed in serial sections of the lungs of mice injected with rAAV2-ESGHGYF (SEQ ID NO:9) (data not shown).

READINGS

[1] Barst et al., 2004 J Am Coll Cardiol, 43: 40-47
[2] McLaughlin et al., 2009, Circulation, 119: 2250-2294
[3] Stenmark et al., 2009, Am J Physiol Lung Cell Mol Physiol, 297: 1013-1032
[4] Friedman et al., 2012 J Obes, 2012: 505274
[5] Chin et al., 2005 Coron Artery Dis., 16: 13-18.
[6] Hemnes et al., 2008 Int J Clin Pract Suppl: 11-19
[7] Humbert et al., 2009 Am J Respir Crit Care Med, 179: 650-656
[8] Simonneau et al., 2009 J Am Coll Cardiol, 54: 43-54
[9] Humbert et al., 2006, Am J Respir Crit Care Med, 173: 1023-1030
[10] Tenenbaum et al. 2003, Curr Gene Ther 3: 545-565
[11] Work et al., 2006, Mol Ther, 4: 683-693
[12] Shi et al., 2006 Hum Gene Ther, 17: 353-361
[13] US 2007/0172460 A1
[14] Michelfelder et al., 2009 PLOS one, 4(4): e5122
[15] Shi and Bartlett, 2003, Mol Ther, 7: 515-525
[16] Loiler et al., 2003, Gene Ther, 10: 1551-1558
[17] Rabinowitz et al., 1999, Virology, 265: 274-285
[18] Wu et al., 2000, J Virol, 74: 8635-8647
[19] Shi et al., 2001, Hum Gene Ther, 12: 1697-1711
[20] Warrington et al. 2004, J Virol, 78: 6595-6609
[21] Girod et al. 1999, Nat Med, 5: 1052-1056
[22] Grifman et al. 2001, Mol Ther, 3: 964-975
[23] Opie et al., 2003, J Virol, 77: 6995-7006
[24] Kern et al., 2003, J Virol, 77: 11072-11081
[25] Russell et al., 1998, J Virol, 72: 309-319
[26] Muller et al., 2003, Nat Biotechnol 21, 1040-1046
[27] Water Kamp, et al., 2006 J Gene Med 8, 1307-1319
[28] Xiao et al., 1998, Journal of Virology 72, 2224-2232
[29] Zolotukhin, et al., 1999, Gene Ther 6, 973-985
[30] McCarty et al., 2001, Gene Ther 8, 1248-1254
[31] Michelfelder, et al., 2007, Exp Hematol 35, 1766-1776
[32] Rohr et al., 2005 J Virol Methods 127, 40-45

The invention claimed is:

1. A capsid protein of a viral vector comprising the amino acid sequence of SEQ ID NO: 1.

2. The capsid protein according to claim 1, which has the amino acid sequence of SEQ ID NO: 2, or a variant thereof which differs from the amino acid sequence of SEQ ID NO: 2 by a modification of one or both of the amino acids located in positions 1 and 2 of the N-terminus of the amino acid sequence of SEQ ID NO:2.

3. The capsid protein according to claim 1, which is a capsid protein of an adeno-associated virus (AAV).

4. The capsid protein according to claim 3, which is a capsid protein of an AAV of a serotype selected from the group consisting of serotypes 2, 4, 6, 8, and 9.

5. The capsid protein according to claim 4, which is a capsid protein of an AAV of serotype 2.

6. The capsid protein according to claim 5, which is a VP1 protein of an AAV of serotype 2.

7. The capsid protein according to claim 1, wherein the amino acid sequence of SEQ ID NO:1 is present in the region of amino acids 550-600 of the capsid protein.

8. The capsid protein according to claim 1, comprising the amino acid sequence of SEQ ID NO: 9.

9. A nucleic acid which encodes a capsid protein according to claim 1.

10. A plasmid which comprises a nucleic acid according to claim 9.

11. A recombinant viral vector which comprises a capsid and a transgene packaged therein, wherein the capsid comprises at least one capsid protein comprising the amino acid sequence of SEQ ID NO: 1 or SEQ ID NO: 2, or a variant thereof which differs from the amino acid sequence of SEQ ID NO: 2 by modification of one or both of the amino acids located in positions 1 and 2 of the N-terminus of the amino acid sequence of SEQ ID NO: 2.

12. The recombinant viral vector according to claim 11, which is a recombinant AAV vector.

13. The recombinant AAV vector according to claim 12, which is an AAV vector of a serotype selected from the group consisting of serotypes 2, 4, 6, 8, and 9.

14. The recombinant AAV vector according to claim 13, which is an AAV vector of serotype 2.

15. The recombinant AAV vector according to claim 11, wherein the transgene encodes a nitric oxide synthase or the bone morphogenic protein receptor 2 (BMPR2).

16. The recombinant AAV vector according to claim 15, wherein the transgene encodes endothelial nitric oxide synthase (eNOS) or inducible nitric oxide synthase (iNOS).

17. The recombinant AAV vector according to claim 11, wherein the transgene is in the form of an ssDNA or a dsDNA.

18. The recombinant AAV vector according to claim 11, for use in a method for the treatment of a lung disorder or a lung disease in a subject.

19. The recombinant AAV vector for use in a method according to claim 18, wherein the lung disease is pulmonary hypertension or pulmonary arterial hypertension.

20. The recombinant AAV vector for use in a method according to claim 18, wherein the subject is a mammal.

21. The recombinant AAV vector for use in a method according to claim 18, wherein the vector is formulated for intravenous administration.

22. A cell which comprises a capsid protein according to claim 1.

23. A pharmaceutical composition which comprises a capsid protein according to claim 1.

24. The nucleic acid of claim 9, wherein the capsid protein comprises the amino acid sequence of SEQ ID NO:9.

25. The recombinant viral vector of claim 11, wherein the capsid protein comprises the amino acid sequence of SEQ ID NO:9.

* * * * *

SEQUENCE LISTING

<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: Lung-specific Peptide

<400> SEQUENCE: 1

Gly His Gly Tyr Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Lung-specific Peptide

<400> SEQUENCE: 2

Glu Ser Gly His Gly Tyr Phe
1               5

<210> SEQ ID NO 3
<211> LENGTH: 7
<212> TYPE: PRT
<213> ORGANISM: Artificial Sequence
<220> FEATURE:
<223> OTHER INFORMATION: Lung-specific Peptide

<400> SEQUENCE: 3

Ala Asp Gly Val Met Trp Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Lung-specific Peptide

<400> SEQUENCE: 4

Gly Glu Val Tyr Val Ser Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Lung-specific Peptide

<400> SEQUENCE: 5

Asn Asn Val Arg Thr Ser Glu
1               5

<210> SEQ ID NO 6
<211> LENGTH: 735
<212> TYPE: PRT
<213> ORGANISM: adeno-associated virus 2

<400> SEQUENCE: 6

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

```
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 7
<211> LENGTH: 598
<212> TYPE: PRT
<213> ORGANISM: adeno-associated virus 2

<400> SEQUENCE: 7

Met Ala Pro Gly Lys Lys Arg Pro Val Glu His Ser Pro Val Glu Pro
1               5                   10                  15

Asp Ser Ser Gly Thr Gly Lys Ala Gly Gln Pro Ala Arg Lys
                20                  25                  30

Arg Leu Asn Phe Gly Gln Thr Gly Asp Ala Asp Ser Val Pro Asp Pro
            35                  40                  45

Gln Pro Leu Gly Gln Pro Pro Ala Ala Pro Ser Gly Leu Gly Thr Asn
        50                  55                  60
```

-continued

```
Thr Met Ala Thr Gly Ser Gly Ala Pro Met Ala Asp Asn Asn Glu Gly
 65                  70                  75                  80

Ala Asp Gly Val Gly Asn Ser Ser Gly Asn Trp His Cys Asp Ser Thr
                 85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Ser Glu Tyr Ser Trp Thr Gly Ala
        355                 360                 365

Thr Lys Tyr His Leu Asn Gly Arg Asp Ser Leu Val Asn Pro Gly Pro
370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
450                 455                 460

Pro Gly Met Val Trp Gln Asp Arg Asp Val Tyr Leu Gln Gly Pro Ile
465                 470                 475                 480
```

```
Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
        500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
        530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
                580                 585                 590

Tyr Leu Thr Arg Asn Leu
                595

<210> SEQ ID NO 8
<211> LENGTH: 533
<212> TYPE: PRT
<213> ORGANISM: adeno-associated virus 2

<400> SEQUENCE: 8

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255
```

-continued

```
Arg Leu Gln Phe Ser Gln Ala Gly Ala Ser Asp Ile Arg Asp Gln Ser
                260                 265                 270
Arg Asn Trp Leu Pro Gly Pro Cys Tyr Arg Gln Arg Val Ser Lys
            275                 280                 285
Thr Ser Ala Asp Asn Asn Ser Glu Tyr Ser Trp Thr Gly Ala Thr
        290                 295                 300
Lys Tyr His Leu Asn Gly Arg Asp Ser Leu Val Asn Pro Gly Pro Ala
305                 310                 315                 320
Met Ala Ser His Lys Asp Asp Glu Glu Lys Phe Phe Pro Gln Ser Gly
                325                 330                 335
Val Leu Ile Phe Gly Lys Gln Gly Ser Glu Lys Thr Asn Val Asp Ile
            340                 345                 350
Glu Lys Val Met Ile Thr Asp Glu Glu Ile Arg Thr Thr Asn Pro
        355                 360                 365
Val Ala Thr Glu Gln Tyr Gly Ser Val Ser Thr Asn Leu Gln Arg Gly
        370                 375                 380
Asn Arg Gln Ala Ala Thr Ala Asp Val Asn Thr Gln Gly Val Leu Pro
385                 390                 395                 400
Gly Met Val Trp Gln Asp Arg Asp Val Tyr Leu Gln Gly Pro Ile Trp
                405                 410                 415
Ala Lys Ile Pro His Thr Asp Gly His Phe His Pro Ser Pro Leu Met
            420                 425                 430
Gly Gly Phe Gly Leu Lys His Pro Pro Pro Gln Ile Leu Ile Lys Asn
        435                 440                 445
Thr Pro Val Pro Ala Asn Pro Ser Thr Thr Phe Ser Ala Ala Lys Phe
450                 455                 460
Ala Ser Phe Ile Thr Gln Tyr Ser Thr Gly Gln Val Ser Val Glu Ile
465                 470                 475                 480
Glu Trp Glu Leu Gln Lys Glu Asn Ser Lys Arg Trp Asn Pro Glu Ile
                485                 490                 495
Gln Tyr Thr Ser Asn Tyr Asn Lys Ser Val Asn Val Asp Phe Thr Val
            500                 505                 510
Asp Thr Asn Gly Val Tyr Ser Glu Pro Arg Pro Ile Gly Thr Arg Tyr
        515                 520                 525
Leu Thr Arg Asn Leu
    530

<210> SEQ ID NO 9
<211> LENGTH: 744
<212> TYPE: PRT
<213> ORGANISM: adeno-associated virus 2

<400> SEQUENCE: 9

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
```

-continued

Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
        130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Gln Arg Gly Glu Ser Gly
                580                 585                 590

His Gly Tyr Phe Ala Gln Ala Ala Thr Ala Asp Val Asn Thr Gln Gly
                595                 600                 605

Val Leu Pro Gly Met Val Trp Gln Asp Arg Asp Val Tyr Leu Gln Gly
610                 615                 620

Pro Ile Trp Ala Lys Ile Pro His Thr Asp Gly His Phe His Pro Ser
625                 630                 635                 640

Pro Leu Met Gly Gly Phe Gly Leu Lys His Pro Pro Pro Gln Ile Leu
                645                 650                 655

Ile Lys Asn Thr Pro Val Pro Ala Asn Pro Ser Thr Thr Phe Ser Ala
                660                 665                 670

Ala Lys Phe Ala Ser Phe Ile Thr Gln Tyr Ser Thr Gly Gln Val Ser
                675                 680                 685

Val Glu Ile Glu Trp Glu Leu Gln Lys Glu Asn Ser Lys Arg Trp Asn
690                 695                 700

Pro Glu Ile Gln Tyr Thr Ser Asn Tyr Asn Lys Ser Val Asn Val Asp
705                 710                 715                 720

Phe Thr Val Asp Thr Asn Gly Val Tyr Ser Glu Pro Arg Pro Ile Gly
                725                 730                 735

Thr Arg Tyr Leu Thr Arg Asn Leu
                740

<210> SEQ ID NO 10
<211> LENGTH: 8359
<212> TYPE: DNA
<213> ORGANISM: adeno-associated virus 2

<400> SEQUENCE: 10

```
catcatcaat aatataccttt attttggatt gaagccaata tgataatgag ggggtggagt      60
ttgtgacgtg gcgcggggcg tgggaacggg gcgggtgacg tagtagctct agaggtcctg     120
tattagaggt cacgtgagtg ttttgcgaca ttttgcgaca ccatgtggtc acgctgggta     180
tttaagcccg agtgagcacg cagggtctcc attttgaagc gggaggtttg aacgcgcagc     240
cgccatgccg gggttttacg agattgtgat taaggtcccc agcgaccttg acgagcatct     300
gcccggcatt tctgacagct tgtgaactg gtggccgag aaggaatggg agttgccgcc     360
agattctgac atggatctga atctgattga gcaggcaccc ctgaccgtgg ccgagaagct     420
gcagcgcgac tttctgacgg aatggcgccg tgtgagtaag caccggagg cccttttctt     480
tgtgcaattt gagaagggag agagctactt ccacatgcac gtgctcgtgg aaaccaccgg     540
ggtgaaatcc atggttttgg gacgtttcct gagtcagatt cgcgaaaaac tgattcagag     600
aatttaccgc gggatcgagc cgactttgcc aaactggttc gcggtcacaa agaccagaaa     660
tggcgccgga ggcgggaaca aggtggtgga tgagtgctac atccccaatt acttgctccc     720
caaaacccag cctgagctcc agtgggcgtg gactaatatg gaacagtatt taagcgcctg     780
```

-continued

```
tttgaatctc acggagcgta aacggttggt ggcgcagcat ctgacgcacg tgtcgcagac      840
gcaggagcag aacaaagaga atcagaatcc caattctgat gcgccggtga tcagatcaaa      900
aacttcagcc aggtacatgg agctggtcgg gtggctcgtg gacaagggga ttacctcgga      960
gaagcagtgg atccaggagg accaggcctc atacatctcc ttcaatgcgg cctccaactc     1020
gcggtcccaa atcaaggctg ccttggacaa tgcgggaaag attatgagcc tgactaaaac     1080
cgcccccgac tacctggtgg gccagcagcc cgtggaggac atttccagca atcggattta     1140
taaaattttg gaactaaacg ggtacgatcc ccaatatgcg gcttccgtct ttctgggatg     1200
ggccacgaaa aagttcggca agaggaacac catctggctg tttgggcctg caactaccgg     1260
gaagaccaac atcgcggagg ccatagccca cactgtgccc ttctacgggt gcgtaaactg     1320
gaccaatgag aactttccct tcaacgactg tgtcgacaag atggtgatct ggtgggagga     1380
ggggaagatg accgccaagg tcgtggagtc ggccaaagcc attctcggag gaagcaaggt     1440
gcgcgtggac cagaaatgca agtcctcggc ccagatagac ccgactcccg tgatcgtcac     1500
ctccaacacc aacatgtgcg ccgtgattga cgggaactca acgaccttcg aacaccagca     1560
gccgttgcaa gaccggatgt tcaaatttga actcacccgc cgtctggatc atgactttgg     1620
gaaggtcacc aagcaggaag tcaaagactt tttccggtgg gcaaaggatc acgtggttga     1680
ggtggagcat gaattctacg tcaaaaaggg tggagccaag aaaagacccg cccccagtga     1740
cgcagatata agtgagccca acgggtgcg cgagtcagtt gcgcagccat cgacgtcaga     1800
cgcggaagct tcgatcaact acgcagacag gtaccaaaac aaatgttctc gtcacgtggg     1860
catgaatctg atgctgtttc cctgcagaca atgcgagaga atgaatcaga attcaaatat     1920
ctgcttcact cacggacaga aagactgttt agagtgcttt cccgtgtcag aatctcaacc     1980
cgtttctgtc gtcaaaaagg cgtatcgaaa actgtgctac attcatcata tcatgggaaa     2040
ggtgccagac gcttgcactg cctgcgatct ggtcaatgtg gatttggatg actgcatctt     2100
tgaacaataa atgatttaaa tcaggtatgg ctgccgatgg ttatcttcca gattggctcg     2160
aggacactct ctctgaagga ataagacagt ggtggaagct caaacctggc ccaccaccac     2220
caaagcccgc agagcggcat aaggacgaca gcaggggtct tgtgcttcct gggtacaagt     2280
acctcggacc cttcaacgga ctcgacaagg gagagccggt caacgaggca gacgccgcgg     2340
ccctcgagca cgacaaagcc tacgaccggc agctcgacag cggagacaac ccgtacctca     2400
agtacaacca cgccgacgcg gagtttcagg agcgccttaa agaagatacg tcttttgggg     2460
gcaacctcgg acgagcagtc ttccaggcga aaaagagggt tcttgaacct ctgggcctgg     2520
ttgaggaacc tgttaagacg gctccgggaa aaaagaggcc ggtagagcac tctcctgtgg     2580
agccagactc ctcctcggga accggaaagg cgggccagca gcctgcaaga aaaagattga     2640
attttggtca gactggagac gcagactcag tacctgaccc ccagcctctc ggacagccac     2700
cagcagcccc ctctggtctg gaactaata cgatggctac aggcagtggc gcaccaatgg     2760
cagacaataa cgagggcgcc gacggagtgg gtaattcctc gggaaattgg cattgcgatt     2820
ccacatggat gggcgacaga gtcatcacca ccagcacccg aacctgggcc ctgcccacct     2880
acaacaacca cctctacaaa caatttccag ccaatcagg agcctcgaac gacaatcact     2940
actttggcta cagcaccccc tggggtatt ttgacttcaa cagattccac tgccactttt     3000
caccacgtga ctggcaaaga ctcatcaaca caactggggg attccgaccc aagagactca     3060
acttcaagct ctttaacatt caagtcaaag aggtcacgca gaatgacggt acgacgacga     3120
ttgccaataa ccttaccagc acggttcagg tgtttactga ctcggagtac cagctcccgt     3180
```

```
acgtcctcgg ctcggcgcat caaggatgcc tcccgccgtt cccagcagac gtcttcatgg    3240
tgccacagta tggataccte accctgaaca acgggagtca ggcagtagga cgctcttcat    3300
tttactgcct ggagtacttt ccttctcaga tgctgcgtac cggaaacaac tttaccttca    3360
gctacacttt tgaggacgtt cctttccaca gcagctacgc tcacagccag agtctggacc    3420
gtctcatgaa tcctctcatc gaccagtacc tgtattactt gagcagaaca aacactccaa    3480
gtggaaccac cacgcagtca aggcttcagt tttctcaggc cggagcgagt gacattcggg    3540
accagtctag gaactggctt cctggaccct gttaccgcca gcagcgagta tcaaagacat    3600
ctgcggataa caacaacagt gaatactcgt ggactggagc taccaagtac cacctcaatg    3660
gcagagactc tctggtgaat ccgggcccgg ccatggcaag ccacaaggac gatgaagaaa    3720
agttttttcc tcagagcggg gttctcatct tgggaagca aggctcagag aaaacaaatg    3780
tggacattga aaggtcatg attacagacg aagaggaaat caggacaacc aatcccgtgg    3840
ctacggagca gtatggttct gtatctacca acctccagag aggccagaga ggcgagtctg    3900
gtcatggtta ttttgcccag gcggccaccg cagatgtcaa cacacaaggc gttcttccag    3960
gcatggtctg gcaggacaga gatgtgtacc ttcaggggcc catctgggca aagattccac    4020
acacggacgg acattttcac ccctctcccc tcatgggtgg attcggactt aaacaccctc    4080
ctccacagat tctcatcaag aacaccccgg tacctgcgaa tccttcgacc accttcagtg    4140
cggcaaagtt tgcttccttc atcacacagt actccacggg acaggtcagc gtggagatcg    4200
agtgggagct gcagaaggaa acagcaaac gctggaatcc cgaaattcag tacacttcca    4260
actacaacaa gtctgttaat gtggacttta ctgtggacac taatgcgtg tattcagagc    4320
ctcgccccat tggcaccaga tacctgactc gtaatctgta attgcttgtt aatcaataaa    4380
ccgtttaatt cgtttcagtt gaactttggt ctctgcgtat ttctttctta tctagttttcc    4440
atgctctaga ggtcctgtat tagaggtcac gtgagtgttt gcgacatttt gcgacacca    4500
tgtggtcacg ctgggtattt aagcccgagt gagcacgcag gtctccatt ttgaagcggg    4560
aggtttgaac gcgcagccac cacggcgggg ttttacgaga ttgtgattaa ggtccccagc    4620
gaccttgacg agcatctgcc cggcattct gacagctttg tgaactgggt ggccgagaag    4680
gaatgggagt tgccgccaga ttctgacatg gatctgaatc tgattgagca ggcaccctg    4740
accgtggccg agaagctgca tcgctggcgt aatagcgaag aggcccgcac cgatcgccct    4800
tcccaacagt tgcgcagcct gaatggcgaa tggcgattcc gttgcaatgg ctggcggtaa    4860
tattgttctg gatattacca gcaaggccga tagtttgagt tcttctactc aggcaagtga    4920
tgttattact aatcaaagaa gtattgcgac aacggttaat ttgcgtgatg gacagactct    4980
tttactcggt ggcctcactg attataaaaa cacttctcag gattctggcg taccgttcct    5040
gtctaaaatc cctttaatcg gcctcctgtt tagctcccgc tctgattcta acgaggaaag    5100
cacgttatac gtgctcgtca aagcaaccat agtacgcgcc ctgtagcggc gcattaagcg    5160
cggcgggtgt ggtggttacg cgcagcgtga ccgctacact tgccagcgcc ctagcgcccg    5220
ctcctttcgc tttcttccct tcctttctcg ccacgttcgc cggctttccc cgtcaagctc    5280
taaatcgggg gctcccttta gggttccgat ttagtgcttt acggcacctc gaccccaaaa    5340
aacttgatta gggtgatggt tcacgtagtg gccatcgccc tgatagacg ttttcgcc     5400
ctttgacgtt ggagtccacg ttctttaata gtggactctt gttccaaact ggaacaacac    5460
tcaaccctat ctcggtctat tcttttgatt tataagggat tttgccgatt tcggcctatt    5520
ggttaaaaaa tgagctgatt taacaaaat ttaacgcgaa ttttaacaaa atattaacgt    5580
```

```
ttacaattta aatatttgct tatacaatct tcctgttttt ggggcttttc tgattatcaa    5640
ccggggtaca tatgattgac atgctagttt tacgattacc gttcatcgat tctcttgttt    5700
gctccagact ctcaggcaat gacctgatag cctttgtaga gacctctcaa aaatagctac    5760
cctctccggc atgaatttat cagctagaac ggttgaatat catattgatg gtgatttgac    5820
tgtctccggc ctttctcacc cgtttgaatc tttacctaca cattactcag gcattgcatt    5880
taaaatatat gagggttcta aaattttta tccttgcgtt gaaataaagg cttctcccgc    5940
aaaagtatta cagggtcata atgttttttgg tacaaccgat ttagctttat gctctgaggc    6000
tttattgctt aattttgcta attctttgcc ttgcctgtat gatttattgg atgttggaat    6060
tcctgatgcg gtattttctc cttacgcatc tgtgcggtat ttcacaccgc atatggtgca    6120
ctctcagtac aatctgctct gatgccgcat agtaagcca gccccgacac ccgccaacac    6180
ccgctgacgc gccctgacgg gcttgtctgc tcccggcatc cgcttacaga caagctgtga    6240
ccgtctccgg gagctgcatg tgtcagaggt tttcaccgtc atcaccgaaa cgcgcgagac    6300
gaaagggcct cgtgatacgc ctattttat aggttaatgt catgataata atggtttctt    6360
agacgtcagg tggcactttt cggggaaatg tgcgcggaac ccctatttgt ttattttct    6420 aaatacattc aaatatgtat ccgctcatga gacaataacc ctgataaatg cttcaataat    6480
attgaaaaag gaagagtatg agtattcaac atttccgtgt cgcccttatt ccctttttg    6540 cggcattttg ccttcctgtt tttgctcacc cagaaacgct ggtgaaagta aaagatgctg    6600
aagatcagtt gggtgcacga gtgggttaca tcgaactgga tctcaacagc ggtaagatcc    6660
ttgagagttt tcgccccgaa gaacgttttc caatgatgag cacttttaaa gttctgctat    6720
gtggcgcggt attatcccgt attgacgccg ggcaagagca actcggtcgc cgcatacact    6780
attctcagaa tgacttggtt gagtactcac cagtcacaga aaagcatctt acggatggca    6840
tgacagtaag agaattatgc agtgctgcca taaccatgag tgataacact gcggccaact    6900
tacttctgac aacgatcgga ggaccgaagg agctaaccgc ttttttgcac aacatggggg    6960
atcatgtaac tcgccttgat cgttgggaac cggagctgaa tgaagccata ccaaacgacg    7020
agcgtgacac cacgatgcct gtagcaatgg caacaacgtt gcgcaaacta ttaactggcg    7080
aactacttac tctagcttcc cggcaacaat taatagactg gatggaggcg gataaagttg    7140
caggaccact tctgcgctcg gcccttccgg ctggctggtt tattgctgat aaatctggag    7200
ccggtgagcg tgggtctcgc ggtatcattg cagcactggg gccagatggt aagccctccc    7260
gtatcgtagt tatctacacg acggggagtc aggcaactat ggatgaacga aatagacaga    7320
tcgctgagat aggtgcctca ctgattaagc attggtaact gtcagaccaa gtttactcat    7380
atatacttta gattgattta aaacttcatt tttaatttaa aaggatctag gtgaagatcc    7440
tttttgataa tctcatgacc aaaatccctt aacgtgagtt ttcgttccac tgagcgtcag    7500
accccgtaga aaagatcaaa ggatcttctt gagatccttt ttttctgcgc gtaatctgct    7560
gcttgcaaac aaaaaaacca ccgctaccag cggtggtttg tttgccggat caagagctac    7620
caactctttt tccgaaggta actggcttca gcagagcgca gataccaaat actgtccttc    7680
tagtgtagcc gtagttaggc caccacttca agaactctgt agcaccgcct acatacctcg    7740
ctctgctaat cctgttacca gtggctgctg ccagtggcga taagtcgtgt cttaccgggt    7800
tggactcaag acgatagtta ccggataagg cgcagcggtc gggctgaacg gggggttcgt    7860
gcacacagcc cagcttggag cgaacgacct acaccgaact gagataccta cagcgtgagc    7920
tatgagaaag cgccacgctt cccgaaggga gaaaggcgga caggtatccg gtaagcggca    7980
```

```
gggtcggaac aggagagcgc acgagggagc ttccagggggg aaacgcctgg tatctttata      8040
gtcctgtcgg gtttcgccac ctctgacttg agcgtcgatt tttgtgatgc tcgtcagggg      8100
ggcggagcct atggaaaaac gccagcaacg cggcctttttt acggttcctg gccttttgct      8160
ggccttttgc tcacatgttc tttcctgcgt tatcccctga ttctgtggat aaccgtatta      8220
ccgcctttga gtgagctgat accgctcgcc gcagccgaac gaccgagcgc agcgagtcag      8280
tgagcgagga agcggaagag cgcccaatac gcaaaccgcc tctccccgcg cgttggccga      8340
ttcattaatg cagaattcc                                                   8359
```

<210> SEQ ID NO 11
<211> LENGTH: 56
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (18)..(38)
<223> OTHER INFORMATION: n is a, c, g, or t

<400> SEQUENCE: 11

```
cagtcggcca gagaggcnnn nnnnnnnnnn nnnnnnnngc ccaggcggct gacgag       56
```

<210> SEQ ID NO 12
<211> LENGTH: 16
<212> TYPE: DNA
<213> ORGANISM: Artificial Sequence
<220> FEATURE:
<223> OTHER INFORMATION: PCR Primer

<400> SEQUENCE: 12

```
ctcgtcagcc gcctgg                                                    16
```

<210> SEQ ID NO 13
<211> LENGTH: 26
<212> TYPE: DNA
<213> ORGANISM: Artificial Sequence
<220> FEATURE:
<223> OTHER INFORMATION: PCR Primer

<400> SEQUENCE: 13

```
gcagtatggt tctgtatcta ccaacc                                         26
```

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14

```
gcctggaaga acgccttgtg tg                                             22
```

<210> SEQ ID NO 15
<211> LENGTH: 22
<212> TYPE: DNA
<213> ORGANISM: Artificial Sequence
<220> FEATURE:
<223> OTHER INFORMATION: PCR Primer

<400> SEQUENCE: 15

```
atggcaagcc acaaggacga tg                                             22
```

```
<210> SEQ ID NO 16
<211> LENGTH: 22
<212> TYPE: DNA
<213> ORGANISM: Artificial Sequence
<220> FEATURE:
<223> OTHER INFORMATION: PCR Primer

<400> SEQUENCE: 16
cgtggagtac tgtgtgatga ag                                              22

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
ggttctcatc tttgggaagc aag                                             23

<210> SEQ ID NO 18
<211> LENGTH: 21
<212> TYPE: DNA
<213> ORGANISM: Artificial Sequence
<220> FEATURE:
<223> OTHER INFORMATION: PCR Primer

<400> SEQUENCE: 18
tgatgagaat ctgtggagga g                                               21

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
ggcggagttg ttacgacat                                                  19

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
gggactttcc ctacttggca                                                 20

<210> SEQ ID NO 21
<211> LENGTH: 7
<212> TYPE: PRT
<213> ORGANISM: Artificial Sequence
<220> FEATURE:
<223> OTHER INFORMATION: control peptide

<400> SEQUENCE: 21

Cys Val Gly Ser Pro Cys Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Peptide from library
```

```
<400> SEQUENCE: 22

Gly Gln Ile Gly Gly Ser Ala
1               5

<210> SEQ ID NO 23
<211> LENGTH: 7
<212> TYPE: PRT
<213> ORGANISM: Artificial Sequence
<220> FEATURE:
<223> OTHER INFORMATION: Peptide from library

<400> SEQUENCE: 23

Leu Thr Arg Ala Ala Gly Val
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide from library

<400> SEQUENCE: 24

Val Pro Trp Ser Pro Ser Val
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide from library

<400> SEQUENCE: 25

Asn Asp Val Arg Ala Val Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide from library
<220> FEATURE:
<221> NAME/KEY: misc_feature
<222> LOCATION: (6)..(6)
<223> OTHER INFORMATION: Xaa can be any naturally occurring amino acid

<400> SEQUENCE: 26

Asn Gln Val Gly Ser Xaa Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide from library

<400> SEQUENCE: 27

Asn Ser Val Ala Ala Thr Ala
1               5

<210> SEQ ID NO 28
<211> LENGTH: 7
<212> TYPE: PRT
<213> ORGANISM: Artificial Sequence
```

```
<220> FEATURE:
<223> OTHER INFORMATION: Peptide from library

<400> SEQUENCE: 28

Pro Arg Thr Leu Ala Glu Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Peptide from library

<400> SEQUENCE: 29

Thr Leu Arg Glu Gln Ser Pro
1               5

<210> SEQ ID NO 30
<211> LENGTH: 7
<212> TYPE: PRT
<213> ORGANISM: Artificial Sequence
<220> FEATURE:
<223> OTHER INFORMATION: Peptide from library

<400> SEQUENCE: 30

Glu Gly Arg Leu Gly Ala Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Peptide from library

<400> SEQUENCE: 31

Gly Gly Arg Pro Met His Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Peptide from library

<400> SEQUENCE: 32

Asn Ser Val Asn Asp Arg Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Peptide from library

<400> SEQUENCE: 33

Pro Arg Ser Val Asp Leu Ser
1               5

<210> SEQ ID NO 34
<211> LENGTH: 7
<212> TYPE: PRT
<213> ORGANISM: Artificial Sequence
```

```
<220> FEATURE:
<223> OTHER INFORMATION: Peptide from library

<400> SEQUENCE: 34

Arg Gly Asp Val Thr Lys Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Peptide from library

<400> SEQUENCE: 35

Gln Gly Asp Leu Gly Leu Ser
1               5
```